US007589254B2

(12) United States Patent
Heim et al.

(10) Patent No.: US 7,589,254 B2
(45) Date of Patent: Sep. 15, 2009

(54) TRANSGENIC EXPRESSION CASSETTES FOR EXPRESSING NUCLEIC ACID SEQUENCES IN SINK TISSUES OF PLANTS THAT STORE CARBOHYDRATE

(75) Inventors: Ute Heim, Gatersleben (DE); Karin Herbers, Quedlinburg (DE); Uwe Sonnewald, Quedlinburg (DE)

(73) Assignee: SunGene GmbH & Co. KGaA (DE)

( * ) Notice: Subject to any disclaimer, the term of this patent is extended or adjusted under 35 U.S.C. 154(b) by 255 days.

(21) Appl. No.: 10/527,375

(22) PCT Filed: Sep. 5, 2003

(86) PCT No.: PCT/EP03/09855

§ 371 (c)(1), (2), (4) Date: Mar. 10, 2005

(87) PCT Pub. No.: WO2004/024926

PCT Pub. Date: Mar. 25, 2004

(65) Prior Publication Data

US 2005/0273888 A1 Dec. 8, 2005

(30) Foreign Application Priority Data

Sep. 10, 2002 (DE) ................................ 102 42 204

(51) Int. Cl.
*C12N 15/63* (2006.01)
*C12N 15/82* (2006.01)
*C12N 15/11* (2006.01)
*A01H 5/00* (2006.01)
*A23L 3/00* (2006.01)

(52) U.S. Cl. ....................... 800/287; 800/286; 800/298; 435/468; 435/410; 435/320.1; 536/23.1; 536/24.1; 426/531; 426/665

(58) Field of Classification Search ....................... None
See application file for complete search history.

(56) References Cited

U.S. PATENT DOCUMENTS

| | | | | |
|---|---|---|---|---|
| 5,436,393 | A | 7/1995 | Rocha-Sosa et al. | |
| 5,608,150 | A | 3/1997 | Conner | |
| 5,859,330 | A | 1/1999 | Bestwick et al. | |
| 6,127,179 | A | 10/2000 | DellaPenna et al. | |
| 6,235,971 | B1 * | 5/2001 | Barry et al. ................. | 800/278 |
| 6,403,371 | B1 * | 6/2002 | Conrad et al. ............ | 435/320.1 |

FOREIGN PATENT DOCUMENTS

| | | |
|---|---|---|
| CA | 2 348 888 | 5/2000 |
| EP | 0 375 092 | 6/1990 |
| WO | WO-91/19806 | 12/1991 |
| WO | WO-98/40503 | 9/1998 |
| WO | WO-00/26338 | 5/2000 |
| WO | WO-00/66610 | 11/2000 |

OTHER PUBLICATIONS

Kim et al 1994, Plant Molecular Biology 24:105-117.*
Donald et al 1990, EMBO J. 9:1717-1726.*
Dolferus et al 1994, Plant Physiology 105:1075-1087.*
Bevan et al. (1986) Nucl Acids Res 14, pp. 4625-4638.
Salanoubat, Marcel et al. "Molecular Cloning and Sequencing of Sucrose Synthase cDNA From Potato (*Solanum tuberosum* L.): Preliminary Characterization of Sucrose Synthase mRNA Distribution" (1987) Gene 60, pp. 47-56.
Deickmann, Jill et al. "Ineraction Of A DNA Binding Factor With The 5'-Flanking Region Of An Ethylene-Responsive Fruit Ripening Gene From Tomato" (1988) EMBO Journal 7, pp. 3315-3320.
Salanoubat, Marcel et al. "The Steady-State Level Of Potato Sucrose Synthase mRNA Is Dependent On Wounding, Anaerobiosis And Sucrose Concentration" (1989), Gene 84, pp. 181-185.
Brisson, Normand, et al., "Maturation And Subcellular Compartmentation Of Potato Starch Phosphorylase" (1989) The Plant Cell 1(5), pp. 559-566.
Rocha-Sosa, Mario et al. "Both Developmental And Metabolic Signals Activate The Promoter Of A Class I Patatin Gene" (1989), EMBO Journal 8, pp. 23-29.
Pear, Julie R. et al. "Isolation And Characterization Of A Fruit-Specific cDNA And The Corresponding Genomic Clone From Tomato" (1989) Plant Molecular Biology 13, pp. 639-651.
Jefferson, Richard et al. "Transcriptional Regulation Of A Patatin-1 Gene Potato" (1990) Plant Molecular Biology 14, pp. 995-1006.
Müller-Röber, Bernd Thomas et al. "One Of Two Different ADP-glucose Pyrophosphorylase Genes From Potato Responds Strongly To Elevated Levels of Sucrose" (1990) Mol Gen Genet 224, pp. 136-146.
Hannapel, David J. "Differential Expression Of Potato Tuber Protein Genes" (1990) Plant Physiol, 94, pp. 919-925.
Baumlein, Helmut et al. "A Novel Seed Protein Gene From *Vicia faba* Is Developmentally Regulated In Transgenic Tobacco And *Arabidopsis* Plants" (1991) Mol Gen Genet 225, pp. 459-467.
Lin, Ershen et al. "Fruit Developmental Regulation Of The Kiwifruit Actinidin Promoter Is Conserved In Transgenic Petunia Plants" (1993) Plant Molecular Biology 23, pp. 489-499.
Sonnewald, Uwe et al. "A Second L-type Isozyme Of Potato Glucan Phosphorylase: Cloning, Antisense Inhibition And Expression Analysis" (1995) Plant Molecular Biology 27, pp. 567-576.
St-Pierre, Benoit et al. "5' Deletion Analysis Of The Potato Starch Phosphorylase Gene: An Upstream Sequence Defines Distal Regulatory Elements And A Proximal Organ-Dependent Promoter" (1995) Plant Science 110(2), pp. 193-203.

(Continued)

*Primary Examiner*—Russell Kallis
*Assistant Examiner*—Brent Page
(74) *Attorney, Agent, or Firm*—Connolly Bove Lodge & Hutz LLP

(57) ABSTRACT

The invention relates to methods for the directed, transgenic expression of nucleic acid sequences in the carbohydrate-storing sink tissues of plants using transgenic expression cassettes which comprise the *Vicia faba* plastidic 1,4-α-D-glucan:phosphate α-D-glucosyltransferase promoter. Furthermore, the invention relates to said transgenic expression cassettes and to transgenic expression vectors and transgenic organisms comprising them, and to the use of the same for the production of foodstuffs, feedstuffs, seed, pharmaceuticals or fine chemicals.

24 Claims, 5 Drawing Sheets

OTHER PUBLICATIONS

Buchner, Peter et al. "Glucan Phosphorylases in *Vicia fala* L.: Cloning, Structural Analysis And Expression Patterns Of Cytosolic And Plastidic Forms In Relation To Starch" (1996) Planta 199, pp. 64-73.

St-Pierre, Benoit et al. "The Starch Phosphorylase Gene Is Subjected To Different Modes Of Regulation In Starch-Containing Tissues Of Potato" (1996) Plant Molecular Biology 30, pp. 1087-1098.

Mette, M.F. et al. "Production Of Aberrant Promoter Transcripts Contributes To Methylation And Silencing Of Unlinked Homologous Promoters *in trans*" (1999) EMBO Journal 18, pp. 241-248.

Buchner, P. et al. "*Vicia faba* var. minor mRNA for alpha 1,4glucan phosphorylase L isoform precursor (VfPhol gene)" GenBank Accession No. Z36880, Apr. 2, 2003.

* cited by examiner

A

B

TRANSGENIC EXPRESSION CASSETTES FOR EXPRESSING NUCLEIC ACID SEQUENCES IN SINK TISSUES OF PLANTS THAT STORE CARBOHYDRATE

RELATED APPLICATIONS

This application is a national stage application (under 35 U.S.C. 371) of PCT/EP2003/009855 filed Sep. 5, 2003, which claims benefit of German application 102 42 204.4 filed Sep. 10, 2002.

The invention relates to methods for the directed, transgenic expression of nucleic acid sequences in the carbohydrate-storing sink tissues of plants using transgenic expression cassettes which comprise the *Vicia faba* plastidic 1,4-α-D-glucan:phosphate α-D-glucosyltransferase promoter. Furthermore, the invention relates to said transgenic expression cassettes and to transgenic expression vectors and transgenic organisms comprising them, and to the use of the same for the production of foodstuffs, feedstuffs, seed, pharmaceuticals or fine chemicals.

The aim of plant biotechnology work is the generation of plants with improved properties, for example for increasing agricultural productivity. Transcriptional regulatory sequences or promoters which regulate the expression of genes in plants are essential elements of plant biotechnology. Various promoters which have been used successfully for the expression of heterologous genes in plants are available; they comprise not only plant promoters (such as, for example, cauliflower heat shock protein hsp80 promoters; U.S. Pat. No. 5,612,472), but also promoters from other non-plant sources such as, for example, promoters of plant viruses (for example the cauliflower mosaic virus 35S promoter) or of plant-infecting bacteria (for example the promoter of the *agrobacterium* octopine synthase; Leisner and Gelvin (1988) Proc Natl Acad Sci USA 85(8):2553-2557).

Frequently, what are known as constitutive promoters, which regulate, in the plant, the expression of a gene product largely at any time and in any tissue are employed for the expression of heterologous nucleic acid sequences in transgenic plants. A directed expression of genes in specific plant parts or at specific points in time of the development is not possible using these promoters. Thus, the protein to be expressed transgenically is expressed at locations and at times where it is not required, which, for example, unnecessarily consumes energy, causes metabolic modifications and can thus have an adverse effect on plant growth. For reasons of product licensing and product acceptance too, it is desirable to express a transgenic protein only where it is required owing to its intended effect.

Tissue- and development-specific promoters are of great interest for this purpose. Various such promoters are known. Thus, the promoter of the *Vicia faba* "sucrose-binding-protein-like gene" (SBP) mediates strong and specific expression in seeds of oilseed rape and other plants (WO 00/26388).

Fruits, seeds, beets/swollen tap roots or tubers, being important storage organs of plant organisms, are of great agronomical relevance. They serve for the storage of proteins, oils and carbohydrates (in particular starch). As a rule, such tissues are photosynthetically inactive and are also referred to as sink tissues or sink organs. They rely on the import of photoassimilates from the photosynthetically active plant parts (source organs or source tissues). Both traditional breeding and biotechnological methods have been used for improving specific aspects of fruit and tuber quality. High-quality, mature fruits are the result of a number of coordinated biochemical and metabolic modifications which can occur not only during maturation, but also during fruit development. These modifications determine the final quality and the quantity of the fruits. Examples of modified properties, for example in the case of tomato fruits, are increased sucrose import, conversion into starch, accumulation of various organic acids, modifications of pigments and modifications in fungicidal and insecticidal compounds. Such results can be achieved by means of the overexpression of genes/proteins or by inhibition by means of double-stranded RNA, antisense RNA or cosuppression. Since sink tissues act as storage site of the most important plant raw materials, promoters which make possible a selective expression in these tissues are of particular interest in plant biotechnology since they permit a directed modification of these tissues and of their constituents.

The skilled worker is familiar with a variety of promoters which can be used for the expression of nucleic acid sequences in fruits, seeds or tubers. The promoter of the tomato genomic clone 2A11 must be mentioned (Pear et al. (1989) Plant Mol Biol 13:639-651; Wo 91/19806). However, the 2A11 promoter governs expression during the very early stages and is relatively weak. The tomato ethylene-inducible E4 and E8 promoters (U.S. Pat. No. 5,859,330; Deickmann et al. (1988) EMBO J. 7:3315-3320) and the polygalacturonase promoter (U.S. Pat. No. 6,127,179) have likewise been described as being fruit-specific. The abovementioned promoters, however, show expression only during the late phases of fruit development, and their use is therefore only limited. The promoters TFM7 and TFM9 (U.S. Pat. No. 5,608,150) are active during fruit development in green and yellow stages. The fruit-specific regulation of the kiwi fruit actinidin promoter has been detected for expression in petunia (Lin et al. (1993) Plant Mol Biol 23:489-499). Thi-1, MADS2 and a promoter fusion between Thi-1 and the melon actin promoter regulate the expression of heterologous genes specifically in apples (WO 00/66610).

Further promoters are, for example, promoters with specificity for tubers, storage roots or other roots such as, for example, the tuber-specific patatin class I promoter (Bevan et al. (1986) Nucl Acids Res 14:4625-4638), the potato cathepsin D inhibitor promoter, the starch synthase (GBSS1) promoter or the sporamin promoter. Other genes with specific high activity in tubers are, for example, the promoter of the ADP-glucose pyrophosphorylase gene (Müller et al. (1990) Mol Gen Genet 224:136-146), of sucrose synthase (Salanoubat and Belliard (1987) Gene 60:47-56; Salanoubat and Belliard (1989) Gene 84:181-185), the promoters of the 22 kD protein complex and of the proteinase inhibitor (Hannapel (1990) Plant Physiol 94:919-925) and the other class I patatins (B33) (EP-A1 0 375 092; Rocha-Sosa et al. (1989) EMBO J. 8:23-29). A disadvantage of the patatin 1 promoter is that it is induced by high sucrose concentrations, also in tissues other than the tuber (Jefferson, R. et al. (1990) Plant Mol Biol 14:995-1006).

Glucan phosphorylases (systematic name: 1,4-α-D-glucan:phosphate α-D-glucosyltransferase; frequently also starch phosphorylase; EC 2.4.1.1) are found in all organisms which are capable of storing starch or glycogen. The enzyme cleaves terminal α-1,4-linked glucose residues from glucan-like molecules with formation of glucose-1-phosphate. Two enzymes exist in plant cells which differ with regard to their localization and specificity for glucans. The Pho2 isoform is located in the cytosol and has high affinity with branched polyglucans such as soluble starch or glycogen. The isoform Pho1 is localized in the stroma of the plastids and prefers unbranched glucan-like amylose and maltodextrins as substrate. Two homologous genes of this isoform with 81% identity have been found in potatoes, the first being expressed predominantly in tubers and the second in leaves (Sonnewald et al. (1995) Plant Mol Biol 27:567-576). Also, two isoforms were isolated from the field bean, *Vicia faba* (Pho1 and Pho2; Buchner P et al. (1996) Planta 199:64-73). The plastidic isoform Pho1 is probably involved in the storage of starch biosynthetic pathway and is expressed to a high degree in essentially the late stages of field bean seed development. Despite the large number of studies into structural and kinetic properties of the plant glucan phosphorylases and their distribution in the various tissues, their precise role in carbohydrate metabolism is unclear. The promoter of a potato gene which encodes a protein with 75% homology to the *Vicia faba* glucan phosphorylase is described (St-Pierre B & Brisson N (1995) Plant Science 110:193-203; St-Pierre et al. (1996) Plant Mol Biol 30:1087-1098). Said promoter shows not only activity in the tubers, but also an activity in the roots which is up to 1.5 times higher than in the tubers. Likewise, high activity was found in the petioles and in the shoot. In total, the activity in the tubers was less than in petioles, in the shoot, in the stolons and in the roots.

The promoters described in the prior art have one or more of the following disadvantages:

1) The promoters do not show the desired expression level and/or are active in a few plant species only.
2) The promoters are only active very early or very late during fruit or tuber development.
3) The expression pattern does not agree with what has been expected, i.e. for example undesired expression activities in other tissues are found.
4) The expression of many of the abovementioned promoters is ethylene-dependent.

Moreover, the number of existing promoters is greatly limited. This may become a limiting factor, in particular in approaches which require the expression of more than one heterologous nucleic acid sequence. The expression, under the same promoter, of different heterologous sequences, in one plant organism can result in "switching off" ("epigenic silencing") of the transgenic expression cassettes in question (Mette et al. (1999) EMBO J. 18:241-248).

It was therefore an object to provide novel promoters and transgenic expression cassettes derived therefrom which have high specificity for sink tissues or sink organs and high activity over as long as possible a development period. This object is achieved by the present invention.

A first subject of the invention relates to methods for the directed, transgenic expression of nucleic acid sequences in carbohydrate-storing sink tissues of plants, which comprises the following steps:

I. Introducing, into plant cells, a transgenic expression cassette, where the transgenic expression cassette comprises at least the following elements:
   a) at least one promoter sequence of the gene encoding the *Vicia faba* plastidic 1,4-α-D-glucan:phosphate α-D-glucosyltransferase, and
   b) at least one further nucleic acid sequence, and
   c) if appropriate, further genetic control elements,
   where at least one of said promoter sequences and one further nucleic acid sequence are functionally linked with one another and the further nucleic acid sequence is heterologous with regard to the promoter sequence, and
II. selection of transgenic cells which comprise said expression cassette stably integrated into the genome, and
III. regeneration of intact plants from said transgenic cells, where at least one of the further nucleic acid sequence is expressed in carbohydrate-storing sink tissue, but essentially not in source tissues.

A further subject relates to transgenic expression cassettes as can be used for example in the method according to the invention. Preferably, the transgenic expression cassettes for the directed, transgenic expression of nucleic acid sequences in the carbohydrate-storing sink tissues of plants comprise a) at least one promoter sequence of the gene encoding the *Vicia faba* plastidic 1,4-α-D-glucan:phosphate α-D-glucosyltransferase, and
b) at least one further nucleic acid sequence, and
c) if appropriate, further genetic control elements, where at least one promoter sequence and one further nucleic acid sequence are functionally linked with one another and the further nucleic acid sequence is heterologous with regard to the promoter sequence.

In a preferred embodiment of the method according to the invention and/or the expression cassettes according to the invention, "promoter sequence of a gene encoding the *Vicia faba* plastidic 1,4-α-D-glucan:phosphate α-D-glucosyltransferase" means promoter sequences which comprise at least one sequence selected from the group of sequences consisting of i) the promoter sequence of SEQ ID NO: 1 and
ii) functionally equivalent promoter sequences which have at least 40% homology with the sequence of SEQ ID NO: 1 over a sequence segment of at least 100 base pairs and which have essentially the same promoter activity as the promoter sequence of SEQ ID NO: 1, and
iii) functionally equivalent fragments of the promoter sequence of i) or ii) with a length of at least 100 base pairs and essentially the same promoter activity as the promoter sequence of SEQ ID NO: 1.

The expression cassettes according to the invention may comprise further genetic control sequences and/or additional functional elements.

Preferably, the transgenic expression cassettes can make possible, owing to the nucleic acid sequence to be expressed transgenically, the expression of a protein encoded by said nucleic acid sequence and/or the expression of a sense RNA, antisense RNA or double-stranded RNA encoded by said nucleic acid sequence.

A further subject of the invention relates to transgenic expression vectors which comprise one of the expression cassettes according to the invention.

A further subject of the invention relates to transgenic organisms which comprise one of the expression cassettes or expression vectors according to the invention. The organism can be selected from the group consisting of bacteria, yeasts, fungi, nonhuman animal organisms and plant organisms or cells, cell cultures, parts, tissues, organs or propagation material derived therefrom; preferably, the organism is selected from the group of the agricultural useful plants. In said plants, the expression of the nucleic acid sequence to be expressed transgenically is preferably higher in at least one sink tissue, preferably in a carbohydratestoring sink tissue (for example the potato tuber or the tomato fruit) than in another tissue.

A further subject of the invention therefore relates to an isolated nucleic acid sequence comprising the promoter of the *Vicia faba* plastidic 1,4-α-D-glucan:phosphate α-D-glucosyltransferase of SEQ ID NO: 1 or a functionally equivalent fragment of same with essentially the same promoter activity.

In a preferred embodiment, the nucleic acid sequence according to the invention, or the transgenic expression cassette according to the invention in the form of a functionally equivalent promoter sequence, additionally comprises the sequence encoding the 5'-untranslated region of the *Vicia*

*faba* Pho1 gene in addition to the sequence of SEQ ID NO: 1. Especially preferred is the sequence described by SEQ ID NO: 2.

In a further preferred embodiment, the nucleic acid sequence according to the invention, or the transgenic expression cassette according to the invention in the form of a functionally equivalent promoter sequence, additionally comprises, in addition to the sequence of SEQ ID NO: 1, the sequence encoding the 5'-untranslated region of the *Vicia faba* Pho1 gene and a sequence encoding a transit peptide, preferably the transit peptide of the *Vicia faba* Pho1 protein of SEQ ID NO: 8. This sequence is preferably in 3'-orientation relative to one of the promoters according to the invention. Especially preferred as promoter sequence in this context is the sequence described by SEQ ID NO: 3.

A further subject relates to the use of the isolated nucleic acid sequences, transgenic expression vectors or transgenic organisms according to the invention for the transgenic expression of nucleic acids and/or proteins. Especially preferred is the use of said transgenic organisms or of cells, cell cultures, parts, tissues, organs or propagation material derived therefrom for the production of foodstuffs, feedstuffs, seed, pharmaceuticals or fine chemicals, the fine chemicals preferably being enzymes, vitamins, amino acids, sugars, saturated or unsaturated fatty acids, natural or synthetic flavorings, aroma substances or colorings. Furthermore comprised by the invention are methods for the production of said foodstuffs, feedstuffs, seed, pharmaceuticals or fine chemicals using the transgenic organisms according to the invention or cells, cell cultures, parts, tissues, organs or propagation material derived therefrom.

Surprisingly, the promoter of the plastidic 1,4-α-D-glucan: phosphate α-D-glucosyltransferase (hereinbelow "Pho1 promoter") from the field bean *Vicia faba* shows high-level, selective expression in carbohydrate-storing sink tissues, such as the potato tubers, beets/swollen tap roots and in fruits, for example tomato. Thus, for example, high-level expression can be found in the potato tuber and tomato fruit, while no discernible expression activity was detected in the seeds of oilseed rape or *Arabidopsis*. The expression activity correlates to a surprising degree with the location/extent of starch biosynthesis or the starch content.

The promoter according to the invention has no homology whatsoever with the known promoter of a putative starch phosphorylase from potato (St-Pierre B & Brisson N (1995) Plant Science 110:193-203; St-Pierre et al. (1996) Plant Mol Biol 30:1087-1098). In addition to an activity in the tubers, the potato starch phosphorylase promoter has an activity in the roots which is up to 1.5 times higher than in the tubers. Likewise, high activities were found in the petioles and in the shoot. In total, the activity in the tubers was less than in petioles, in the shoot, in the stolons and in the roots. In contrast, the *Vicia faba* Pho1 promoter according to the invention has the advantage that, besides the surprisingly high activity in the potato tubers and in the tomato fruits, only very low activities, or none, were found in other tissues. FIG. 2 shows the tissue-specific expression of the Pho1 promoter during fruit development in tomatoes. Only little activity was detected in the leaves and the roots. The promoter is at its most active in young green fruits; this activity decreases as the fruit ripens.

The USP promoter (Baumlein et al. (1991) Mol Gen Genet 225:459-467) was studied in comparison. Surprisingly, β-glucuronidase (GUS) expression experiments showed high-level expression in the potato tubers and in the tomato fruits for the Pho1 promoter only, while no expression was found for the USP promoter. Accordingly, there is no inherent linkage between expression in seeds and carbohydrate-storing sink tissue.

Expression, brought about by the Pho1 promoter, is high, in particular in immature, green fruits, and decreases in the maturing, red fruits. Here, the expression level correlates with the starch content (cf. FIG. 2 vs. FIG. 4). A similar correlation can also be found in potatoes, but in this case the starch is accumulated only when the tuber has reached the adult stage, and it is here that the promoter shows its maximum activity. No significant expression was detected in other tissues.

Owing to its high expression activity and its high specificity, the Pho1 promoter according to the invention is particularly valuable for plant biotechnology. It can be expected that the Pho1 promoter will also be active in carbohydrate- and/or storage-starch-containing tissues of other plants. In particular the fact that its activity has an early onset during organ development can be exploited advantageously for increasing the quality of the developing fruit. Very especially advantageous in this context is the use in approaches which serve for the modification of carbohydrate and/or starch biosynthesis or of the carbohydrate and/or starch metabolism. Examples of nucleic acid sequences to be expressed by preference in this context are given hereinbelow.

"Expression" means the transcription of the nucleic acid sequence to be expressed transgenically, but can—in the case of an open reading frame in sense orientation—also include the translation of the transcribed RNA, of the nucleic acid sequence to be expressed transgenically, into a corresponding polypeptide.

"Transgenic" means—for example regarding a transgenic expression cassette, a transgenic expression vector, a transgenic or ganism or method for the transgenic expression of nucleic acids all those constructs which are the result of transgenic methods, or all methods using them, in which either a) the Pho1 promoter of SEQ ID NO: 1, 2 or 3 a functionally equivalent fragment of the above, or
b) the nucleic acid sequence to be expressed transgenically, in functional linkage with a promoter of a), or
c) (a) and (b)

are not located in their natural genetic environment or have been modified by transgenic methods, where the modification can be for example a substitution, addition, deletion, inversion or insertion of one or more nucleotide residues. Preferably, the promoter sequence according to the invention which is present in the expression cassettes (for example the sequence of SEQ ID NO: 1, 2 or 3) is heterologous with regard to the further nucleic acid sequence which is linked functionally with it and which is to be expressed transgenically. In this context, "heterologous" means that the further nucleic acid sequence does not encode the gene which is naturally under the control of said promoter.

"Natural genetic environment" means the natural chromosomal locus in the organism of origin or the presence in a genomic library. In the case of a genomic library, the natural genetic environment of the nucleic acid sequence is preferably retained at least in part. The environment flanks the nucleic acid sequence at least at one side and has a sequence length of at least 50 bp, preferably at least 500 bp, especially preferably at least 1000 bp, very especially preferably at least 5000 bp. A naturally occurring expression construct—for example the naturally occurring combination of the promoter of SEQ ID NO: 1 and the coding sequence of the 1,4-α-D-glucan:phosphate α-D-glucosyltransferase gene from the field bean *Vicia faba* becomes a transgenic expression construct when this combination is modified by normatural, synthetic ("artificial") methods such as, for example, an in-vitro mutagenesis. Such methods have been described (U.S. Pat. No. 5,565,350; WO 00/15815; see also hereinabove).

"Transgenic" with regard to an expression ("transgenic expression") preferably means all those expressions which have been carried out using a transgenic expression cassette, transgenic expression vector or transgenic organism, as defined hereinabove.

"Directed" with regard to the expression in carbohydrate-storing sink tissues means that the expression under the control of one of the promoters according to the invention in the carbohydratestoring sink tissues amounts to preferably at least ten times, very especially preferably to at least fifty times, most preferably to at least hundred times the expression level in another tissue, preferably in a source tissue such as, for example, the leaves.

The transgenic expression cassettes according to the invention, the transgenic expression vectors and transgenic organisms derived from them can comprise functional equivalents of the Pho1 promoter sequence described in SEQ ID NO: 1. Said functional equivalents have at least 40%, preferably at least 60%, especially preferably at least 80%, very especially preferably at least 90% homology with the sequence of SEQ ID NO: 1 over a sequence segment of at least 100 base pairs, preferably at least 200 base pairs, very especially preferably at least 500 base pairs, most preferably over the entire sequence length, and have essentially the same promoter activity as the promoter sequence of SEQ ID NO: 1.

The transgenic expression cassettes according to the invention, the transgenic expression vectors and transgenic organisms derived from them can comprise functionally equivalent fragments of the promoter of SEQ ID NO: 1 or of a functional equivalent of the same. To prepare such functionally equivalent fragments, it is possible, for example, to delete nonessential sequences of a promoter according to the invention without adversely affecting the abovementioned essential properties to a significant extent. Such deletion variants constitute functionally equivalent fragments of the Pho1 promoter described by SEQ ID NO: 1 or of a functional equivalent of the same. The delimitation of the promoter sequence to certain, essential regulatory regions can be carried out for example with the aid of search routines for the search of promoter elements. Frequently, certain promoter elements are amassed in the regions which are relevant for the promoter activity. This analysis can be carried out for example with computer programs such as the program PLACE ("Plant Cis-acting Regulatory DNA Elements") (Higo K et al. (1999) Nucl Acids Res 27(1): 297-300) or the BIOBASE database "Transfac" (Biologische Datenbanken GmbH, Braunschweig).

Preferably, the functionally equivalent fragments of one of the promoters according to the invention—for example the Pho1 promoter described by SEQ ID NO: 1 or of a functional equivalent thereof—comprise at least 100 base pairs, very especially preferably at least 200 base pairs, most preferably at least 500 base pairs of the Pho1 promoter described by SEQ ID NO: 1 or of a functional equivalent thereof. In a preferred embodiment, the functionally equivalent fragment comprises the 3' region of the Pho1 promoter described by SEQ ID NO: 1 or of a functional equivalent thereof, the fragment length which is in each case preferred being calculated in 5' direction upstream from the transcription start or translation start ("ATG" codon).

A promoter activity is referred to as essentially the same when the transcription of a certain gene to be expressed under the control of, for example, a functional equivalent fragment of the Pho1 promoter sequence described by SEQ ID NO: 1 under otherwise unchanged conditions—in at least one sink tissue, preferably in a carbohydrate-storing, -sythesizing or -metabolizing sink tissue (such as, for example, the potato tuber, beet and tomato fruit), very especially preferably in a starch-storing, -sythesizing or -metabolizing sink tissue (such as, for example, the potato tuber), is higher than in another tissue, for example a source tissue.

In this context, "carbohydrate" preferably means starch or sucrose, especially preferably starch.

"Source tissue" means photosynthetically active tissue. "Sink tissue" means tissues which are net importers of photosynthetically fixed carbon dioxide and which, as a rule, are not photosynthetically active. Examples of sink tissues which may be mentioned are: roots, fruits, tubers and seed kernels.

Starch-storing sink tissue (hereinbelow "starch sink tissue") preferably means those tissues which a) are not photosynthetically active themselves and
b) have at at least one point in time of their development a starch content which can be detected by means of a starch detection reaction. A preferred starch detection reaction is staining with Lugol's solution (Lugol's solution: for example: dissolve 2 g of KI in 5 ml of water, dissolve 1 g of iodine in this solution and add 300 ml of water). Staining, is carried out until a discernible blue coloration has appeared (approximately 15 minutes at RT) and can be stopped by washing with water.

Here, the expression under the control of one of the promoters according to the invention in a carbohydrate-storing, -synthesizing or -metabolizing sink tissue or a starch sink tissue is preferably at least twice, very especially preferably at least five times, most preferably at least ten times as high as in another tissue, for example a source tissue.

Sequences which are preferably employed when determining the expression level are those which code readily quantifiable proteins. Very especially preferred in this context are reporter proteins (Schenborn E, Groskreutz D. (1999) Mol Biotechnol 13(1): 29-44) such as "green fluorescence protein" (GFP) (Chui W L et al. (1996) Curr Biol 6:325-330; Leffel S M et al. (1997) Biotechniques 23(5):912-8), chloramphenicol transferase, luciferase (Millar et al. (1992) Plant Mol Biol Rep 10:324-414), β-glucuronidase or β-galactosidase. β-Glucuronidase (Jefferson et al. (1987) EMBO J. 6:3901-3907) is very especially preferred.

"Otherwise unchanged conditions" means that the expression which is initiated by one of the transgenic expression cassettes to be compared is not modified by combination with additional genetic control sequences, for example enhancer sequences. Unchanged conditions furthermore means that all framework conditions such as, for example, plant species, developmental stage of the plants, growing conditions, assay conditions (such as buffers, temperature, substrates and the like) are kept identical between the expressions to be compared.

The expression level of a functionally equivalent promoter can deviate both downward and upward compared with the promoter of SEQ ID NO: 1. Preferred in this context are those sequences whose expression level, measured on the basis of the transcribed mRNA or the subsequently translated protein, under conditions which are otherwise unchanged differs quantitatively by not more than 50%, preferably 25%, particularly preferably 10%, from a comparison value obtained with those promoters described by SEQ ID NO: 1. Especially preferred sequences are those whose expression level, measured on the basis of the transcribed mRNA or the subsequently translated protein, under conditions which are otherwise unchanged exceeds quantitatively a comparison value obtained with the promoter described by SEQ ID NO: 1 by more than 50%, preferably 100%, especially preferably 500%, very especially preferably 1000%. Preferred as comparison value is the expression level of the mRNAs of a 1,4-α-D-glucan:phosphate α-D-glucosyltransferase expressed naturally by the promoter, or the protein resulting therefrom. Furthermore preferred as comparison value is the expression level obtained with any defined nucleic acid sequence, preferably those nucleic acid sequences which encode readily quantifiable proteins. Very especially preferred in this context are reporter proteins (Schenborn E & Groskreutz D (1999) Mol Biotechnol 13(1):29-44) such as the "green fluorescence protein" (GFP) (Chui W L et al. (1996) Gurr Biol 6:325-330; Leffel S M et al. (1997) Biotechniques. 23(5):912-8), the chloramphenicol transferase, a luciferase (Millar et al. (1992) Plant Mol Biol Rep 10:324-414) or the β-glucuronidase; β-glucuronidase is very especially preferred (Jefferson et al. (1987) EMBO J. 6:3901-3907).

Functional equivalents also comprise natural or artificial mutations of the promoter sequence described in SEQ ID NO: 1. Mutations comprise substitutions, additions, deletions, inversions or insertions of one or more nucleotide residues. Thus, for example, the present invention also comprises those nucleotide sequences which are obtained by modification of the Pho1 promoter of SEQ ID NO: 1. The aim of such a modification may be the further delimitation of the sequence present therein or else, for example, the introduction or removal of restriction endonuclease cleavage sites, the removal of superfluous DNA or the addition of further sequences, for example further regulatory sequences.

Where insertions, deletions or substitutions such as, for example, transitions and transversions, are suitable it is possible to use techniques known per se, such as in-vitro mutagenesis, primer repair, restriction or ligation. Transition means a base pair exchange of a purine/pyrimidine pair into another purine/pyrimidine pair (for example A-T for G-C). Transversion means a base pair exchange of a purine/pyrimidine pair for a pyrimidine/purine pair (e.g. A-T for T-A). Deletion means removal of one or more base pairs. Insertion means the introduction of one or more base pairs.

Complementary ends of the fragments can be made available for ligation by means of manipulations such as restriction, chewing back or filling in overhangs for what are known as blunt ends. Analogous results can also be obtained using the polymerase chain reaction (PCR) using specific oligonucleotide primers.

Homology between two nucleic acids is understood as meaning the identity of the nucleic acid sequence over the complete sequence length in each case, which is calculated by comparison with the aid of the GAP program algorithm (Wisconsin Package Version 10.0, University of Wisconsin, Genetics Computer Group (GCG), Madison, USA), setting the following parameters:

| | | | |
|---|---|---|---|
| Gap Weight: | 12 | Length Weight: | 4 |
| Average Match: | 2.912 | Average Mismatch: | −2.003 |

For example, a sequence which has at least 50% homology with the sequence SEQ ID NO: 1 on nucleic acid basis is understood as meaning a sequence which, upon comparison with the sequence SEQ ID NO: 1 by the above program algorithm with the above set of parameters has at least 50% homology.

Functional equivalents also means DNA sequences which hybridize under standard conditions with the nucleic acid sequence encoding the Pho1 promoter as shown in SEQ ID NO: 1 or with the nucleic acid sequences complementary thereto, and which have substantially the same promoter properties. The term standard hybridization conditions is to be understood broadly and means both stringent and less stringent hybridization conditions. Such hybridization conditions are described inter alia in Sambrook J, Fritsch E F, Maniatis T et al., in Molecular Cloning—A Laboratory Manual, $2^{nd}$ edition, Cold Spring Harbor Laboratory Press, 1989, pages 9.31-9.57 or in Current Protocols in Molecular Biology, John Wiley & Sons, N.Y. (1989), 6.3.1-6.3.6.

For example, the conditions during the washing step can be selected from the range of conditions limited by those of low stringency (with approximately 2×SSC at 50° C.) and of high stringency (with approximately 0.2×SSC at 0.50° C., preferably at 65° C.) (20×SSC: 0.3 M sodium citrate, 3 M NaCl, pH 7.0). In addition, the temperature during the washing step can be raised from low-stringency conditions at room temperature, approximately 22° C., to more stringent conditions at approximately 65° C. Both parameters, the salt concentration and the temperature, can be varied simultaneously, and it is also possible for one of the two parameters to be kept constant and only the other to be varied. It is also possible to employ denaturing agents such as, for example, form amide or SDS during the hybridization. Hybridization in the presence of 50% formamide is preferably carried out at 42° C. Some exemplary conditions for hybridization and washing steps are given below:

(1) Hybridization conditions with for example
  a) 4×SSC at 65° C., or
  b) 6×SSC, 0.5% SDS, 100 μg/ml denatured fragmented salmon sperm DNA at 65° C., or
  c) 4×SSC, 50% formamide, at 42° C., or
  d) 2× or 4×SSC at 50° C. (low-stringency condition), or
  e) 2× or 4×SSC, 30 to 40% formamide at 42° C. (low-stringency condition), or
  f) 6×SSC at 45° C., or,
  g) 0.05 M sodium phosphate buffer pH 7.0, 2 mM EDTA, 1% BSA and 7% SDS.

(2) Washing steps with for example
  a) 0.1×SSC at 65° C., or
  b) 0.1×SSC, 0.5% SDS at 68° C., or
  c) 0.1×SSC, 0.5% SDS, 50% formamide at 42° C., or
  d) 0.2×SSC, 0.1% SDS at 42° C., or
  e) 2×SSC at 65° C. (low-stringency condition), or
  f) 40 mM sodium phosphate buffer pH 7.0, 1% SDS, 2 mM EDTA.

Methods for preparing functional equivalents of the invention preferably comprise the introduction of mutations into the Pho1 promoter as shown in SEQ ID NO: 1. Mutagenesis may be random, in which case the mutagenized sequences are subsequently screened for their properties by a trial and error procedure. Particularly advantageous selection criteria comprise for example the level of the resulting expression of the introduced nucleic acid sequence in a starch-sink tissue.

Methods for mutagenesis of nucleic acid sequences are known to the skilled worker and include by way of example the use of oligonucleotides with one or more mutations compared with the region to be mutated (e.g. in a site-specific mutagenesis). Primers with approximately 15 to approximately 75 nucleotides or more are typically employed, with preferably about 10 to about 25 or more nucleotide residues being located on both sides of the sequence to be modified. Details and procedure for said mutagenesis methods are familiar to the skilled worker (Kunkel et al. (1987) Methods Enzymol 154:367-382; Tomic et al. (1990) Nucl Acids Res 12:1656; Upender et al. (1995) Biotechniques 18(1):29-30; U.S. Pat. No. 4,237,224). A mutagenesis can also be achieved by treating for example transgenic expression vectors comprising one of the nucleic acid sequences of the invention with mutagenizing agents such as hydroxylamine.

A functional linkage means, for example, the sequential arrangement of one of the promoters according to the invention, of the nucleic acid sequence to be expressed transgenically and, if appropriate, of further regulatory elements such as, for example, a terminator in such a way that each of the regulatory elements is able to fulfill its function, depending on the arrangement of the nucleic acid sequences in relation to sense or antisense RNA, in the transgenic expression of the nucleic acid sequence. This does not necessarily require a direct linkage in the chemical sense. Genetic control sequences such as, for example, enhancer sequences, can also exert their function on the target sequence from positions which are further removed, or indeed from other DNA molecules. Preferred arrangements are those in which the nucleic acid sequence to be expressed transgenically is positioned behind the sequence which acts as promoter so that both sequences are mixed covalently with one another. Preferably, the distance between the promoter sequence and the nucleic acid sequence to be expressed transgenically is less than 200 base pairs, especially preferably less than 100 base pairs, very especially preferably less than 50 base pairs.

A transgenic expression cassette or a functional linkage can be produced by means of conventional recombination and cloning techniques as are described, for example, in Maniatis T et al. (1989) Molecular Cloning: A Laboratory Manual, Cold Spring Harbor Laboratory, Cold Spring Harbor, N.Y. and in Silhavy T J et al. (1984) Experiments with Gene Fusions, Cold Spring Harbor Laboratory, Cold Spring Harbor, N.Y. and in Ausubel F M et al. (1987) Current Protocols in Molecular Biology, Greene Publishing Assoc. and Wiley Interscience. A method which is suitable for this purpose is, for example, the GATEWAY™ cloning technology (Invitrogen Inc.), which is based on recombination.

A transgenic expression cassette according to the invention is prepared for example by fusing one of the promoters according to the invention as shown in SEQ ID NO: 1 (or a functional equivalent or functionally equivalent part thereof) with a nucleotide sequence to be expressed transgenically, if appropriate with a sequence encoding a transit peptide, preferably a chloroplast-specific transit peptide, which is preferably arranged between the promoter and the nucleotide sequence in question, and optionally with a terminator or polyadenylation signal. The combination of the Pho1 promoter with the sequence encoding its natural transit peptide (corresponding to SEQ ID NO: 3) is especially preferred in this context.

However, a transgenic expression cassette also means those constructions in which one of the promoters of the invention is, without having been functionally linked beforehand to a nucleic acid sequence to be expressed transgenically, introduced into a host genome, for example by targeted homologous recombination or random insertion, where it undertakes regulatory control over nucleic acid sequences then functionally linked thereto, and governs the transgenic expression thereof. Insertion of the promoter—for example by a homologous recombination—in front of a nucleic acid encoding for a particular polypeptide results in a transgenic expression cassette of the invention which governs the expression of the particular polypeptide in the plant. Furthermore, the insertion of the promoter may also take place in such a way that antisense RNA to the nucleic acid encoding a certain polypeptide is expressed. Thus, the expression of the particular polypeptide in plants is downregulated or silenced.

The nucleic acid sequences which are present in the transgenic expression cassettes according to the invention and which are to be expressed transgenically can be linked functionally with further genetic control sequences, besides one of the promoters according to the invention.

The concept of the genetic control sequences is to be understood broadly and means all those sequences which have an effect on the origin or the function of the transgenic expression cassette according to the invention. Genetic control sequences modify, for example, the transcription and/or translation in prokaryotic or eukaryotic organisms. Preferably, the transgenic expression cassettes according to the invention comprise one of the promoters according to the invention 5'-upstream from the particular nucleic acid sequence to be expressed transgenically and a terminator sequence 3'-downstream as additional genetic control sequence, and, if appropriate, further customary regulatory elements, in each case functionally linked with the nucleic acid sequence to be expressed transgenically.

Genetic control sequences also comprise further promoters, promoter elements or minimal promoters which are capable of modifying expression-controlling properties. It is thus possible, by means of genetic control sequences, that for example tissue-specific expression takes place in addition in dependence on certain stress factors. Suitable elements are described, for example, for water stress, abscisic acid (Lam E and Chua N H (1991) J Biol Chem 266(26):17131-17135) and heat stress (Schöffl F et al. (1989) Mol Gen Genet (217 (2-3):246-53).

It is furthermore possible that further promoters which make possible expression in further plant tissues or in other organisms such as, for example, *E. coli* bacteria, are linked functionally with the nucleic acid sequence to be expressed. Suitable plant promoters are, in principle, all of the above-described promoters. For example, it is conceivable that a certain nucleic acid sequence is transcribed, in a plant tissue, as sense RNA, and translated into the corresponding protein, by one promoter (for example one of the promoters according to the invention), while the same nucleic acid sequence is, in a different tissue, transcribed into antisense RNA, and the corresponding protein is downregulated, by a different promoter with a different specificity. This can be carried out by means of a transgenic expression cassette according to the invention by positioning the one promoter before the nucleic acid sequence to be expressed transgenically and the other promoter behind it.

Genetic control sequences furthermore also comprise the 5'-untranslated region, introns, the noncoding 3' region or else sequences of genes, preferably the Pho1 gene, which encode signal or transit peptides. It has been shown that these regions may have significant functions in regulating gene expression. Thus, it has been shown that 5'-untranslated sequences are capable of enhancing the transient expression of heterologous genes. Furthermore, they may promote tissue specificity (Rouster J et al. (1998) Plant J 15:435-440). Conversely, the 5'-untranslated region of the opaque-2 gene suppresses expression. Deletion of the region in question results in an increase in gene activity (Lohmer S et al. (1993) Plant Cell 5:65-73).

In transgenic rice cells, the use of the Act1 intron in combination with the 35S promoter led to an expression rate which was increased by a factor of ten in comparison with the isolated 35S promoter (McElroy et al. (1991) Mol Gen Genet 231(1):150-160). An optimization with the sequence environment of the translation initiation site of the GUS reporter gene resulted in a four-fold increase in GUS expression in transformed rice cells. A combination of the optimized translation initiation site and of the Act1 intron resulted in a 40-fold increase in GUS expression by the CaMV35S promoter in transformed rice cells; similar results were obtained with transformed maize cells. In total, the conclusion drawn from the above-described studies was that the expression vectors based on the Act1 promoter are suitable for controlling a sufficiently high-level and constitutive expression of foreign DNA in transformed cells of monocotyledonous plants.

The promoter sequences shown in SEQ ID NO: 2 or 3 comprise the segment of the Pho1 gene which represents the promoter and the 5'-untranslated region up to before the ATG start codon of the Pho1 protein.

The transgenic expression cassette can advantageously comprise one or more of what are known as enhancer sequences in functional linkage with the promoter, which make increased transgenic expression of the nucleic acid sequence possible. Additional advantageous sequences can also be inserted at the 3' end of the nucleic acid sequences to be expressed transgenically, such as further regulatory elements or terminators. The nucleic acid sequences to be expressed transgenically can be present as one or more copies in one of the transgenic expression cassettes according to the invention.

Control sequences are furthermore understood as meaning those which make possible homologous recombination or insertion into the genome of a host organism, or which permit deletion from the genome. In the case of homologous recombination, one of the promoters according to the invention may be substituted for the natural promoter of a particular gene, for example. One of the promoters according to the invention can—as described above—be placed, by means of homologous recombination, before an endogenous target gene to be expressed transgenically, by linking the promoter with DNA sequences which are for example homologous to endogenous sequences located upstream of the reading frame of the target gene. Such sequences are to be understood as genetic control sequences. Methods such as the cre/lox technology permit tissue-specific, and in some circumstances inducible, deletion of the transgenic expression cassette from the genome of the host organism (Sauer B (1998) Methods (Duluth) 14(4): 381-92). Here, certain flanking sequences are added to the target gene (lox sequences), which later make possible deletion by means of cre recombinase.

To select cells which have successfully undergone homologous recombination, or else transformation, it is, as a rule, necessary additionally to introduce a selectable marker (see hereinbelow). Homologous recombination is a relatively rare event in higher eukaryotes, in particular in plants. Random integrations into the host genome predominate. One possibility of deleting the randomly integrated sequences, and thus to increase the concentration of cell clones with a correct homologous recombination, is the use of a sequence-specific recombination system as described in U.S. Pat. No. 6,110,736.

Polyadenylation signals which are suitable as control sequences are plant polyadenylation signals and—preferably—those which essentially correspond to T-DNA polyadenylation signals from *Agrobacterium tumefaciens*. In a particularly preferred embodiment, the transgenic expression cassette comprises a terminator sequence which is functional in plants. Terminator sequences which are functional in plants generally means those sequences which are capable of bringing about, in plants, the termination of the transcription of a DNA sequence. Examples of suitable terminator sequences are the OCS (octopine synthase) terminator and the NOS (nopalin synthase) terminator. However, plant terminator sequences are especially preferred. Plant terminator sequences generally refers to those sequences which are part of a natural plant gene. Especially preferred in this context is the terminator of the potato cathepsin D inhibitor gene (GenBank Acc. No.: X74985) or the terminator of the field bean storage protein gene VfLE1B3 (GenBank Acc. No.: Z26489).

These terminators are at least equivalent to the viral or T-DNA terminators described in the prior art.

Transgenic expression, under the control of the Pho1 promoter, of the proteins encoded by the nucleic acid sequences is possible in any desired cell compartment such as, for example, the endomembrane system, the vacuole and the chloroplasts. By utilizing the secretory pathway, desired glycosylation reactions, especially folding processes, and the like are possible. The signal peptide sequences required as genetic control sequences for this purpose may either already be provided in individual transgenic expression cassettes or else be introduced, into the transgenic expression cassette, jointly with the nucleic acid sequence to be expressed transgenically, by using a suitable cloning strategy.

Signal or transit peptide sequences which can be used are both homologous or heterologous sequences. Additional heterologous sequences which are preferred for functional linkage, but not limited thereto, are further targeting sequences for ensuring subcellular localization in the apoplast, in the vacuole, in plastids, in mitochondria, in the endoplasmic reticulum (ER), in the nucleus, in oil bodies or in other compartments; and translation enhancers such as the tobacco mosaic virus 5' leader sequence (Gallie et al. (1987) Nucl Acids Res 15:8693-8711) and the like. The method for the targeted transportation into the plastids, of proteins which per se are not located in the plastids, is described (Klosgen R B and Weil J H (1991) Mol Gen Genet 225(2):297-304; Van Breusegem F et al. (1998) Plant Mol Biol 38(3):491-496). Preferred sequences are:

a) the transit peptide of the Pho1 protein, b) the transit peptide of the small subunit (SSU) of ribulose-bisphosphatecarboxylase (Rubisco ssu) from, for example, pea, maize or sunflower, c) transit peptides derived from genes of plant fatty acid biosynthesis, such as the transit peptide of the plastidic acyl carrier protein (ACP), stearyl-ACP desaturase, β-ketoacyl-ACP synthase or acyl-ACP thioesterase, d) the GBSSI (granule-bound starch synthase I) transit peptide, e) the transit peptide of the LHCP II genes f) the transketolase transit peptide (EP-A1 0 723 017).

The target sequences can be linked with other targeting sequences which differ from the sequences encoding the transit peptide, in order to ensure subcellular localization in the apoplast, in the vacuole, in plastids, in mitochondria, in the endoplasmic reticulum (ER), in the nucleus, in oil bodies or in other compartments. Furthermore, translation enhancers such as the tobacco mosaic virus 5' leader sequence (Gallie et al. (1987) Nucl Acids Res 15:8693-8711) and the like may be employed.

As already mentioned, the sequence encoding a transit peptide is—in an especially preferred embodiment—already inserted into the cassette or the vector for the preparation of a transgenic expression cassette or a transgenic expression vector. Very especially preferably, this involves the use of constructs which comprise the Pho1 promoter in linkage with a sequence encoding the putative transit peptide of the Pho1 protein (SEQ ID NO: 8). A promoter construct which is preferably used in this context is described by SEQ ID NO: 3. To ensure sufficient processing, this construct comprises sequences encoding approximately a further 10 amino acids behind the transit peptide, thus ensuring efficient processing thereof. In this case, a protein to be expressed transgenically in the plastids would be cloned into the reading frame behind the sequence encoding the transit peptide, in the manner with which the skilled worker is familiar, which would bring about the transgenic expression of a chimeric protein with the Pho1 transit peptide.

The skilled worker is familiar with a multiplicity of nucleic acids or proteins whose expression, controlled by the transgenic expression cassettes according to the invention, is advantageous. Furthermore, the skilled worker is familiar with a multiplicity of genes through whose repression or deletion, by means of transgenic expression of, for example, a suitable double-stranded RNA or an antisense RNA, advantageous effects can likewise be obtained. Suitable for the purposes of the present invention are, in particular, those target genes which play a role in the sugar or starch metabolism, in sink-source relations, in the balance of organic acids, as flavor components, in the resistance to biotic stress factors (pathogens, viruses, insects and diseases), in the resistance to abiotic stress factors (heat, chill, drought, elevated moisture, pollutants, UV radiation), in the consistency of the tissues or in water/pH ratios, in the improvement of food or feed characteristics, the improvement of the germination and/or storage characteristics, and in the improvement of the growth rate or the yield.

Increasing the starch content is of particular interest especially in the case of tomatoes or potatoes. A normal tomato consists of approximately 80 to 95% of water, while starch—as the actually relevant component for the production of, for example, tomato paste, ketchup—is only a minor component. Even a small increase in the starch content would be of considerable economic importance. During the early stages of maturation, the starch content of tomatoes amounts to 20% and is thus markedly higher, whereas later during the development it drops owing to the starch being mobilized and converted into sugars. In potatoes, an increased starch content has advantageous effects in particular on the deep-frying properties.

Nucleic acid sequences whose expression under the control of one of the promoters according to the invention has advantageous effects may be mentioned below by way of example, but not by limitation:

1. Improved protection of the plant to abiotic stress factors such as drought, heat or chill, for example by overexpressing antifreeze polypeptides from Myoxocephalus Scorpius (WO 00/00512), Myoxocephalus octodecemspinosus, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREBlA factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).
2. Expression of metabolic enzymes for use in the food-and-feed sector, for example of phytases and cellulases. Especially preferred are nucleic acids such as the artificial cDNA which encodes a microbial phytase (GenBank Acc. No.: A19451) or functional equivalents thereof.
3. Achieving a resistance, for example to fungi, insects, nematodes and diseases, by targeted secretion or accumulation of certain metabolites or proteins. Examples which may be mentioned are glucosinolates (defense against herbivores), chitinases or glucanases and other enzymes which destroy the cell wall of parasites, ribosome-inactivating proteins (RIPS) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, α-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents of these.

The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (Galanthus nivalis) lectin agglutinin (Rao et al. (1998) Plant J 15(4):469-77).

The expression of synthetic cryIA(b) and cryIA(c) genes, which encode *lepidoptera*-specific *Bacillus thuringiensis* Δ-endotoxins can bring about a resistance to insect pests in various plants (Goyal R K et al. (2000) Crop Protection 19(5): 307-312).

Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164).

4. Expression of genes which bring about an accumulation of fine chemicals such as of tocopherols, tocotrienols or carotenoids. An example which may be mentioned is phytoene desaturase. Preferred are nucleic acids which encode the Narcissus pseudonarcissus photoene desaturase (GenBank Acc. No.: X78815) or functional equivalents thereof.
5. Production of nutraceuticals such as, for example, polyunsaturated fatty acids (for example arachidonic acid, eicosapentaenoic acid or docosahexaenoic acid) by expression of fatty acid elongases and/or desaturases, or production of proteins with improved nutritional value such as, for example, with a high content of essential amino acids (for example the high-methionine 2S albumin gene of the brazil nut). Preferred are nucleic acids which encode the Bertholletia excelsa high-methionine 2S albumin (GenBank Acc. No.: AB044391), the *Physcomitrella patens* Δ6-acyl-lipid desaturase (GenBank Acc. No.: AJ222980; Girke et al. (1998) Plant J 15:39-48), the *Mortierella* alpina Δ6-desaturase (Sakuradani et al. 1999 Gene 238:445-453), the *Caenorhabditis elegans* Δ5-desaturase (Michaelson et al. 1998, FEBS Letters 439:215-218), the *Caenorhabditis elegans* Δ5-fatty acid desaturase (des-5) (GenBank Acc. No.: AF078796), the *Mortierella alpina* Δ5-desaturase (Michaelson et al. JBC 273:19055-19059), the *Caenorhabditis elegans* Δ6-elongase (Beaudoin et al. 2000, PNAS 97:6421-6426), the *Physcomitrella patens* Δ6-elongase (Zank et al. 2000, Biochemical Society Transactions 28:654-657), or functional equivalents of these.

6. Production of high-quality proteins and enzymes for industrial purposes (for example enzymes, such as lipases) or as pharmaceuticals (such as, for example, antibodies, blood clotting factors, interferons, lymphokins, colony stimulation factor, plasminogen activators, hormones or vaccines, as described by Hood E E, Jilka J M (1999) Curr Opin Biotechnol 10(4):382-6; Ma J K, Vine N D (1999) Curr Top Microbiol Immunol 236:275-92). For example, it has been possible to produce recombinant avidin from chicken albumen and bacterial β-glucuronidase (GUS) on a large scale in transgenic maize plants (Hood et al. (1999) Adv Exp Med Biol 464:127-47. Review).
8. Obtaining an increased storability in cells which normally comprise fewer storage proteins or storage lipids, with the purpose of increasing the yield of these substances, for example by expression of acetyl-CoA carboxylase. Preferred nucleic acids are those which encode the *Medicago sativa* acetyl-CoA carboxylase (accase) (GenBank Acc. No.: L25042), or functional equivalents thereof.

Further examples of advantageous genes are mentioned for example in Dunwell J M, Transgenic approaches to crop improvement, J Exp Bot. 2000; 51 Spec No; pages 487-96.

Furthermore, it is possible to express functional analogs of the abovementioned nucleic acids or proteins. In this context, functional analogs means all those sequences which have essentially the same function, i.e. which are capable of exerting the function (for example a substrate conversion or a signal transduction), as the protein mentioned by way of example. In this context, the functional analog may indeed differ with regard to other features. For example, it may have a higher or lower activity or else have further functionalities. Functional analogs furthermore means sequences which encode fusion proteins consisting of one of the preferred proteins and other proteins, for example a further preferred protein, or else a signal peptide sequence.

Furthermore, the skilled worker knows that the above-described genes need not be expressed directly using the nucleic acid sequences encoding these genes or repress these above-described genes, for example by antisense. It is also possible to use for example artificial transcription factors of the zinc finger protein type (Beerli R R et al. (2000) Proc Natl Acad Sci USA 97(4):1495-500). These factors attach in the regulatory regions of the endogenous genes to be expressed or to be repressed and, depending on the design of the factor, bring about an expression or repression of the endogenous gene. Thus, the desired effects can also be achieved by expressing a suitable zinc finger transcription factor under the control of one of the promoters according to the invention.

Likewise, the transgenic expression cassettes according to the invention can be employed for the reduction (suppression) of transcription and/or translation of target genes by "gene silencing". Thus, the transgenic expression cassettes according to the invention can express nucleic acids which bring about PTGS (post transcriptional gene silencing) or TGS (transcriptional silencing) effects and thus a reduction of the expression of endogenous genes. Said reduction can be achieved for example by expression of an antisense RNA (EP-A1 0 458 367; EP-A1 0 140 308; van der Krol A R et al. (1988) BioTechniques 6(10):658-676; de Lange P et al. (1995) Curr Top Microbiol Immunol 197:57-75, inter alia) or of a double-stranded RNA, each of which has homology with the endogenous target gene to be suppressed. Also, the expression of a suitable sense RNA can bring about a reduction of the expression of endogenous genes, by means of what is known as co-suppression (EP-A1 0 465 572). Moreover, further methods such as, for example, the regulation of gene expression by means of viral expression systems (virus-induced gene silencing, VIGS; WO 98/36083, WO 99/15682) exist. Especially preferred is the expression of a double-stranded RNA for reducing the gene expression of a target gene. WO 99/32619 and WO 99/53050 describe methods for inhibiting individual target genes using an RNA with double-stranded structure, where the target gene and the region of the RNA duplex have at least partial identity (see also: Montgomery M K et al. (1998) Proc Natl Acad Sci USA 95:15502-15507; Sharp P A (1999) Genes & Development 13(2):139-141; Fire A et al. (1998) Nature 391:806-11). The method is currently also referred to as RNA interference (RNAi).

Preferred applications where the reduction (suppression) of gene expression brings about an advantageous phenotype comprise by way of example, but not by limitation:

1. Modification of the carbohydrate composition

A modification of the carbohydrate composition can be achieved for example by reducing the gene expression of genes of the carbohydrate metabolism or of carbohydrate biosynthesis, for example the biosynthesis of amylose, pectins, cellulose or cell-wall carbohydrates. A multiplicity of cellular processes (maturation, starch composition, starch content and the like) can thus be influenced in an advantageous manner. Target genes which may be mentioned by way of example, but not by limitation, are phosphorylases, starch synthetases, branching enzymes, sucrose-6-phosphate synthetases, sucrose-6-phosphate phosphatases, lipoxygenases (Griffiths A. et al. (1999) Postharvest Biology & Technology 17(3):163-173), ADP-glucose pyrophosphorylases, branching enzymes, debranching enzymes, and various amylases. The genes in question are described (Dunwell J M (2000) J Exp Botany 51 Spec No: 487-96; Brar D S et al. (1996) Biotech Genet Eng Rev 13:167-79; Kishore G M and Somerville C R (1993) Curr Opin Biotech 4(2):152-8). Advantageous genes for influencing the carbohydrate metabolism—in particular starch biosynthesis are—described in WO 92/11375, WO 92/11376, U.S. Pat. No. 5,365,016 and WO 95/07355.

In a further advantageous embodiment, a shift of the amylose/amylopectin ratio in starch can be brought about by suppression of the two isoforms of the branching enzyme which are responsible for the α-1,6-glycosidic linkage. Such procedures are described (for example by Schwall G P et al. (2000) Nat Biotechnol 18(5):551-554). Nucleic acid sequences such as that of the potato starch branching enzyme II (GenBank Acc. No.: AR123356; U.S. Pat. No. 6,169,226) or its homologs from other genera and species are preferably used for this purpose.

Especially advantageous is the reduction of starch mobilization and conversion into sugars at low temperatures (cold sweetening) by means of reducing the expression of glucan phosphorylase (systematic name: 1,4-α-D-glucan:phosphate α-D-glucosyltransferase; U.S. Pat. No. 5,998,710).

2. Delayed fruit maturation

Delayed fruit maturation or a modified maturation phenotype (prolonged maturation, later senescence) can be achieved for example by reducing the gene expression of genes selected from the group consisting of polygalacturonases, pectin esterases, β-(1,4)glucanases (cellulases), β-galactanases (β-galactosidases), or genes of ethylene biosynthesis, such as 1-aminocyclopropane-1-carboxylate synthase, adenosylmethionine hydrolase (SAMase), aminocyclopropane-1-carboxylate deaminase, aminocyclopropane-1-carboxylate oxidase, genes of carotenoid biosynthesis such as, for example, genes of pre-phytoene biosynthesis or phytoene biosynthesis, for example phytoene desaturases, and O-methyltransferases, acyl carrier protein (ACP), elongation factor, auxin-induced gene, cysteine(thiol) proteinases, starch phosphorylases, pyruvate decarboxylases, chalcone reductases, protein kinases, auxin-related gene, sucrose transporters, meristem pattern gene. Further advantageous genes are described for example in WO 91/16440, WO 91/05865, WO 91/16426, WO 92/17596, WO 93/07275 or WO 92/04456. Especially preferred is the reduction of the expression of polygalacturonase for the prevention of cell degradation and mushiness of plants and fruits, for example tomatoes. Nucleic acid sequences such as that of the tomato polygalacturonase gene (GenBank Acc. No.: x14074) or its homologs are preferably used for this purpose.

3. Improved protection against abiotic stress factors (heat, chill, drought, elevated moisture, pollutants, UV radiation). It is preferred to reduce the expression of genes which are implicated in stress reactions.
4. Reduction of the storage protein content
The reduction of the gene expression of genes encoding storage proteins (hereinbelow SPs) has numerous advantages, such as, for example, the reduction of the allergenic potential or modification regarding composition or quantity of other metabolites, such as, for example, oil or starch content.
5. Obtaining a resistance to plant pathogens
Resistance to plant pathogens such as arachnids, fungi, insects, nematodes, protozoans, viruses, bacteria and diseases can be achieved by reducing the gene expression of genes which are essential for the growth, survival, certain developmental stages (for example pupation) or the multiplication of a specific pathogen. Such a reduction can bring about a complete inhibition of the abovementioned steps, or else a delay of same. They can take the form of plant genes which for example make possible the penetration of the pathogen, but may also be homologous pathogen genes. The transgenically expressed nucleic acid sequence (for example the double-stranded RNA) is preferably directed against genes of the pathogen. The antipathogenic agent which acts may be, in this context, the transgenically expressed nucleic acid sequence itself (for example the double-stranded RNA), but also the transgenic expression cassettes or transgenic organisms. The plants themselves, in the form of a transgenic organism, may contain the agents and pass them on to the pathogens, for example in the form of a stomach poison. Various essential genes of a variety of pathogens are known to the skilled worker (for example for nematode resistance WO 93/10251, WO 94/17194).
6. Most preferred as pathogens are fungal pathogens such as *Phytophthora infestans, Fusarium nivale, Fusarium graminearum, Fusarium culmorum, Fusarium oxysporum, Blumeria graminis, Magnaporthe grisea, Sclerotinia sclerotium, Septoria nodorum, Septoria tritici, Alternaria brassicae, Phoma lingam*, bacterial pathogens such as *Corynebacterium sepedonicum, Erwinia carotovora, Erwinia amylovora, Streptomyces scabies, Pseudomonas syringae* pv. *tabaci, Pseudomonas syringae* pv. *phaseolicola, Pseudomonas syringae* pv. tomato, *Xanthomonas campestris* pv. *malvacearum* and *Xanthomonas campestris* pv. *oryzae*, and nematodes such as *Globodera rostochiensis, G. pallida, Heterodera schachtii, Heterodera avenae, Ditylenchus dipsaci, Anguina tritici* and *Meloidogyne hapla.*
7. Virus resistance can be achieved for example by reducing the expression of a viral coat protein, a viral replicase, a viral protease and the like. A large number of plant viruses and suitable target genes are known to the skilled worker.
8. Reduction of undesired, allergenic or toxic plant constituents such as, for example, glucosinolates or patatin. Suitable target genes are described (in WO 97/16559, inter alia). The target genes which are preferred for reduction of allergenic proteins are described for example by Tada Y et al. (1996) FEBS Lett 391(3):341-345 or Nakamura R (1996) Biosci Biotechnol Biochem 60(8):1215-1221.
9. Delayed signs of senescence. Suitable target genes are, inter alia, cinnamoyl-CoA:NADPH reductases or cinnamoyl-alcohol dehydrogenases. Further target genes are described (in WO 95/07993, inter alia).
10. Reduction of the susceptibility to bruising of, for example, potatoes by reducing for example polyphenol oxidase (WO 94/03607) and the like.
11. Increase of the methionine content by reducing threonine biosynthesis, for example by reducing the expression of threonine synthase (Zeh M et al. (2001) Plant Physiol 127(3):792-802).

Antisense nucleic acid firstly means a nucleic acid sequence which is fully or in part complementary to at least part of the sense strand of said target protein. The skilled worker knows that an alternative is the use of the cDNA or the corresponding gene as starting template for suitable antisense constructs. Preferably, the antisense nucleic acid is complementary to the coding region of the target protein or part of same. However, the antisense nucleic acid may also be complementary to the noncoding region or part of same. Starting from the sequence information of a target protein, an antisense nucleic acid can be designed in the manner with which the skilled worker is familiar, taking into consideration the Watson-Crick base pair rules. An antisense nucleic acid can be complementary to all or part of the nucleic acid sequence of a target protein. In a preferred embodiment, the antisense nucleic acid is an oligonucleotide with a length of, for example, 25, 30, 35, 40, 45 or 50 nucleotides.

The antisense strategy can advantageously be combined with a ribozyme method. Ribozymes are catalytically active RNA sequences which, when linked with the antisense sequences, catalytically cleave the target sequences (Tanner N K (1999) FEMS Microbiol Rev 23(3):257-75). The efficiency of an antisense strategy may thereby be increased. The expression of ribozymes for reducing certain proteins is known to the skilled worker and described for example in EP-A1 0 291 533, EP-A1 0 321 201 and EP A1 0 360 257. Suitable target sequences and ribozymes can be identified for example as described by Steinecke (Ribozymes, Methods in Cell Biology 50, Galbraith et al. eds Academic Press, Inc. (1995), 449-460) by calculating the secondary structures of ribozyme and target RNA and also by their interaction (Bayley C C et al. (1992) Plant Mol Biol 18(2):353-361; Lloyd A M and Davis R W et al. (1994) Mol Gen Genet 242(6):653-657). Examples which may be mentioned are hammerhead ribozymes (Haselhoff and Gerlach (1988) Nature 334:585-591). Preferred ribozymes are based on derivatives of the Tetrahymena L-19 IVS RNA (U.S. Pat. No. 4,987,071; U.S. Pat. No. 5,116,742). Further ribozymes with selectivity for an L119 mRNA can be selected (Bartel D and Szostak J W (1993) Science 261:1411-1418).

Also comprised is the use of the above-described sequences in sense orientation which, as the skilled worker will know, can lead to co-suppression. The expression of sense RNA to an endogenous gene can reduce or eliminate expression thereof, in a similar manner to what has been described for antisense approaches (Goring et al. (1991) Proc Natl Acad Sci USA, 88:1770-1774; Smith et al. (1990) Mol Gen Genet 224:447-481; Napoli et al. (1990) Plant Cell 2:279-289; Van der Krol et al. (1990) Plant Cell 2:291-299). In this context, the construct introduced may represent the gene to be reduced either fully or only in part. No possibility of translation is necessary.

Also very especially preferred is the use of methods such as gene regulation by means of double-stranded RNA (double-stranded RNA interference). Such methods are known to the skilled worker and described in detail (for example Matzke M A et al. (2000) Plant Mol Biol 43:401-415; Fire A. et al. (1998) Nature 391:806-811; WO 99/32619; WO 99/53050; WO 00/68374; WO 00/44914; WO 00/44895; WO 00/49035; WO 00/63364). The methods and processes described in the references cited are expressly referred to. Here, a highly efficient suppression of native genes is brought about by the simultaneous introduction of strand and counterstrand.

The transgenic expression cassettes according to the invention and transgenic expression vectors derived from them may comprise further functional elements. The term functional element is to be understood broadly and means all those elements which have an effect on the generation, multiplication or function of the transgenic expression cassettes according to the invention or on transgenic expression vectors or organisms derived from them. The following may be mentioned by way of example, but not by limitation:

1. Selection Markers

The term "selection marker" comprises not only positive selection markers, which confer a resistance to an antibiotic, herbicide or other biocide, but also negative selection markers, which confer a sensitivity to precisely the abovementioned, and also markers which confer a growth advantage to the transformed organism (for example by expression of key genes of cytokine biosynthesis; Ebinuma H et al. (2000) Proc Natl Acad Sci USA 94:2117-2121). In the case of positive selection, only those organisms which express the selection marker in question thrive, while precisely these organisms die in the case of negative selection. The use of a positive selection marker is preferred in the generation of transgenic plants. Furthermore preferred is the use of selection markers which confer growth advantages. Negative selection markers can be used advantageously when the task at hand consists in eliminating certain genes or genome segments from an organism (for example for the purposes of a hybridization process).

i) Positive Selection Markers:

The selectable marker introduced with the transgenic expression cassette confers resistance to a biocide, for example a herbicide (such as phosphinothricin, glyphosate or bromoxynil), a metabolic inhibitor (such as 2-deoxyglucose-6-phosphate; WO 98/45456) or an antibiotic (such as, for example, tetracyclins, ampicillin, kanamycin, G 418, neomycin, bleomycin or hygromycin) to the successfully transformed cells. The selection marker permits the selection of the transformed cells from untransformed cells (McCormick et al. (1986) Plant Cell Reports 5:81-84.

Especially preferred selection markers are those which confer resistance to herbicides. Selection markers which may be mentioned by way of example are:

DNA sequences which encode phosphinothricin acetyltransferases (PAT) (also referred to as Bialophos® resistance gene (bar)), which acetylate the free amino group of the glutamine synthase inhibitor phosphinothricin (PPT) and thus detoxify the PPT (de Block et al. (1987) EMBO J. 6:2513-2518; Vikkers JE et al. (1996) Plant Mol Biol Reporter 14:363-368; Thompson CJ et al. (1987) EMBO J. 6:2519-2523). The bar/PAT gene can be isolated for example from *Streptomyces hygroscopicus* or *S. viridochromogenes*. Such sequences are known to the skilled worker (*Streptomyces hygroscopicus* GenBank Acc. No.: X17220 and X05822; *Streptomyces* viridochromogenes GenBank Acc. No.: M22827 and X65195; U.S. Pat. No. 5,489,520). Synthetic genes are further described for expression in plastids (GenBank Acc. No.: AJ028212).

5-Enolpyruvylshikimate-3-phosphate synthase genes (EPSP synthase genes), which confer resistance to Glyphosat® (N-(phosphonomethyl)glycin). The nonselective herbicide glyphosate has 5-enolpyruvyl-3-phosphoshikimate synthase (EPSPS) as molecular target. This enzyme has a key function in the biosynthesis of aromatic amino acids in plants (Steinrucken H C et al. (1980) Biochem Biophys Res Commun 94:1207-1212; Levin J G and Sprinson D B (1964) J Biol Chem 239: 1142-1150; Cole D J (1985) Mode of action of glyphosate; A literature analysis, pp. 48-74. In: Grossbard E and Atkinson D (eds.). The herbicide glyphosate. Buttersworths, Boston). Glyphosate-tolerant EPSPS variants are preferably used as selection markers (Padgette S R et al. (1996). New weed control opportunities: development of soybeans with a Roundup Ready gene. In: Herbicide Resistant Crops (Duke S O, ed.), pp. 53-84. CRC Press, Boca Raton, Fla.; Saroha M K and Malik V S (1998) J Plant Biochemistry and Biotechnology 7:65-72). The EPSPS gene of *Agrobacterium* sp. strain CP4 has a natural tolerance to glyphosate which can be transferred to corresponding transgenic plants. The CP4 EPSPS gene has been cloned from *Agrobacterium* sp. strain CP4 (Padgette S R et al. (1995) Crop Science 35(5):1451-1461). 5-Enolpyruvylshikimate-3-phosphate synthases which are glyphosate-tolerant, such as, for example, those described in U.S. Pat. No. 5,510,471; U.S. Pat. No. 5,776,760; U.S. Pat. No. 5,864,425; U.S. Pat. No. 5,633,435; U.S. Pat. No. 5,627,061; U.S. Pat. No. 5,463,175; EP 0 218 571, are preferred, the sequences described in the patents in each case also being deposited in GenBank. Further sequences are described under GenBank Accession X63374. The aroA gene (GenBank Acc. No.: M10947) is furthermore preferred.

the gox gene (glyphosate oxidoreductase), which encodes the Glyphosat®-degrading enzymes. GOX (for example the glyphosate oxidoreductase from *Achromobacter* sp.) catalyzes the cleavage of a C—N bond in glyphosate, which is thus converted into aminomethylphosphonic acid (AMPA) and glyoxylate. GOX can thereby confer resistance to glyphosate (Padgette S R et al. (1996) J Nutr 126(3):702-16; Shah D et al. (1986) Science 233: 478-481).

the deh gene (encoding a dehalogenase which inactivates Dalapon®; WO 99/27116; GenBank Acc. No.: AX022822, AX022820)

bxn genes, which encode Bromoxynil®-degrading nitrilase enzymes, for example the *Klebsiella ozanenae* nitrilase. Sequences can be found in GenBank for example under the Acc. No.: E01313 and J03196.

Neomycin phosphotransferases (npt) confer resistance to antibiotics (aminoglycosides) such as neomycin, G418, hygromycin, paromomycin or kanamycin, by reducing their inhibitory action by means of a phosphorylation reaction. Especially preferred is the nptII gene (GenBank Acc. No.: AF080390; AF080389). Moreover, the gene is already a component in a large number of expression vectors and can be isolated from them using methods with which the skilled worker is familiar (such as, for example, polymerase chain reaction) (GenBank Acc. No.: AF234316 pCAMBIA-2301; AF234315 pCAMBIA-2300, AF234314 pCAMBIA-2201). The NPTII gene encodes an aminoglycoside 3'-O-phosphotransferase from *E. coli*, Tn5 (GenBank Acc. No.: U00004 position 1401-2300; Beck et al. (1982) Gene 19 327-336).

the DOG$^R$1 gene was isolated from the yeast *Saccharomyces cerevisiae* (EP 0 807 836) and it encodes a 2-deoxyglucose-6-phosphate phosphatase, which confers resistance to 2-DOG (Randez-Gil et al. (1995) Yeast 11:1233-1240; Sanz et al. (1994) Yeast 10:1195-1202; GenBank Acc. No.: NC001140 position 194799-194056).

Sulfonylurea- and imidazolinone-inactivating acetolactate synthases, which confer resistance to imidazolinone/sulfonylurea herbicides. Examples which may be mentioned of imidazolinone herbicides are the active substances imazamethabenz-methyl, imazzamox, imazapyr, imazaquin and imazethapyr. Examples of sulfonylurea herbicides which may be mentioned are amidosulforon, azimsulfuron, chlorimuronethyl, chlorsulfuron, cinosulfuron, imazosulforon, oxasulforon, prosulforon, rimsulforon, sulfosulforon. The skilled worker is familiar with a large number of further active substances from the abovementioned classes. The sequence for the *Arabidopsis thaliana* Csr 1.2 gene (EC 4.1.3.18) which has been deposited under the GenBank Acc. No.: X51514, is suitable for example (Sathasivan K et al. (1990) Nucleic Acids Res. 18(8):2188). Acetolactate synthases, which confer resistance to imidazolinone herbicides, are furthermore described under the GenBank Acc. Nos: AB049823, AF094326, X07645, X07644, A19547, A19546, A19545, 105376 (EP 0 257 993), 105.373 (EP 0 257 993), AL133315.

Hygromycin phosphotransferases (e.g. GenBank Acc. No.: X74325) which confer resistance to the antibiotic hygromycin. The gene is a component of a large number of expression vectors and can be isolated from them using methods with which the skilled worker is familiar (such as, for example, polymerase chain reaction) (GenBank Acc. No.: AF294981 pINDEX4; AF234301 pCAMBIA-1380; AF234300 pCAMBIA-1304; AF234299 pCAMBIA-1303; AF234298 pCAMBIA-1302; AF354046 pCAMBIA-1305; AF354045 pCAMBIA-1305.1)

genes for resistance to a) chloramphenicol (chloramphenicol acetyltransferase), b) tetracyclin; various resistance genes have been described, for example GenBank Acc. No.: X65876, X51366. Moreover, the gene is already a component of a large number of expression vectors and can be isolated therefrom using methods known to the skilled worker (such as, for example, polymerase chain reaction)

c) Streptomycin; various resistance genes have been described, for example with the GenBank Acc. No.: AJ278607.

d) Zeocin; the corresponding resistance gene is a component of a large number of cloning vectors (for example GenBank Acc. No.: L36849 cloning vector PZEO) and can be isolated from these using methods known to the skilled worker (such as, for example, polymerase chain reaction).

e) Ampicillin (β-lactamase gene; Datta N, Richmond M H. (1966) Biochem J 98(1):204-9; Heffron F et al. (1975) J. Bacteriol 122:250-256; the Amp gene was first cloned for generating the *E. coli* vector pBR322; Bolivar F et al. (1977) Gene 2:95-114). The sequence is a component of a large number of cloning vectors and can be isolated from them using methods known to the skilled worker (such as, for example, polymerase chain reaction).

Genes such as the isopentenyl transferase from *Agrobacterium tumefaciens* (strain:PO22) (GenBank Acc. No.: AB025109). The ipt gene is a key enzyme of cytokine biosynthesis. Its overexpression facilitates the regeneration of plants (for example selection on cytokine-free medium). The method for utilizing the ipt gene has been described (Ebinuma H et al. (2000) Proc Natl Acad Sci USA 94:2117-2121; Ebinuma H et al. (2000) Selection of marker-free transgenic plants using the oncogenes (ipt, rol A, B, C) of *Agrobacterium* as selectable markers, In Molecular Biology of Woody Plants. Kluwer Academic Publishers).

Various other positive selection markers which confer a growth advantage to the transformed plants over non-transformed plants, and methods for their use, have been described, inter.alia, in EP-A 0 601 092. Examples which may be mentioned are β-glucuronidase (in conjunction with, for example, cytokinin glucuronide), mannose-6-phosphate isomerase (in conjunction with mannose), UDP-galactose 4-epimerase (in conjunction with, for example, galactose), with mannose-6-phosphate isomerase in conjunction with mannose being especially preferred.

ii) Negative Selection Markers

Negative selection markers make possible for example the selection of organisms with successfully deleted sequences which comprise the marker gene (Koprek T et al. (1999) The Plant Journal 19(6):719-726). When carrying out a negative selection, for example a compound which otherwise has no disadvantageous effect on the plant is converted into a compound which is disadvantageous, for example owing to the negative selection marker introduced into the plant. Genes which have a disadvantageous effect per se are furthermore suitable. Negative selection markers which may be mentioned by way of example, but not by limitation, are TK thymidine kinase (TK), diphtheria toxin A fragment (DT-A), the coda gene product encoding a cytosine deaminase (Gleave A P et al. (1999) Plant Mol Biol 40(2):223-35; Perera R J et al. (1993) Plant Mol Biol 23(4): 793-799; Stougaard J (1993) Plant J 3:755-761), the cytochrome P450 gene (Koprek et al. (1999) Plant J 16:719-726), genes encoding a haloalkane dehalogenase (Naested H (1999) Plant J 18:571-576), the iaaH gene (Sundaresan V et al. (1995) Genes & Development 9:1797-1810.) or the tms2 gene (Fedoroff N V & Smith D L (1993) Plant J 3:273-289).

2) Reporter Genes

Reporter genes encode readily quantifiable proteins which, via their color or enzyme activity, allow an assessment of the transformation efficiency, the site or time of expression (see also Schenbron E, Groskreutz D. Mol Biotechnol. 1999; 13(1):29-44). Examples which may be mentioned are:

"green fluorescence protein" (GFP) (Chui W L et al. (1996), Curr Biol 6:325-330; Leffel S M et al. (1997) Biotechniques 23(5):912-8; Sheen et al. (1995) Plant J 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228).

Chloramphenicol transferase (Fromm et al. (1985) Proc Natl Acad Sci USA 82:5824-5828), Luciferase (Millar et al. (1992) Plant Mol Biol Rep 10:324-414; Ow et al. (1986) Science 234:856-859); allows detection via bioluminescence.

β-Galactosidase, encodes an enzyme for which a variety of chromogenic substrates are available.

β-Glucuronidase (GUS) (Jefferson et al. (1987) EMBO J. 6:3901-3907) or the uidA gene, which encodes an enzyme for a variety of chromogenic substrates.

R-Locus gene product: protein which regulates the production of anthocyanine pigments (red coloration) in plant tissue and thus makes possible the direct analysis of the promoter activity without addition of further auxiliary substances or chromogenic substrates (Dellaporta et al. (1988) In: Chromosome Structure and Function: Impact of New Concepts, 18$^{th}$ Stadler Genetics Symposium, 11:263-282).

Tyrosinase (Katz et al. (1983) J Gen Microbiol 129:2703-2714), an enzyme which oxidizes tyrosine to DOPA and dopaquinone, which subsequently form melanin, which can be detected readily.

Aequorin (Prasher et al. (1985) Biochem Biophys Res Commun 126(3):1259-1268), can be used in the calcium-sensitive bioluminescence detection.

3) Replication Origins

Replication origins ensure the multiplication of the transgenic expression cassettes or transgenic expression vectors according to the invention in, for example, *E. coli* or *agrobacteria*. Examples which may be mentioned are OR1 (origin of DNA replication), the pBR322 ori or the P15A ori (Sambrook et al.: Molecular Cloning. A Laboratory Manual, 2$^{nd}$ ed. Cold Spring Harbor Laboratory Press, Cold Spring Harbor, N.Y., 1989). Examples of replication origins which are functional in *Agrobacterium* are pRK2, pRi, PVS1 or pSA.

4) Border Sequences

"Border sequences" (such as, for example, the right or left border of the T-DNA) make possible an *agrobacteria*-mediated transfer into plant cells for the transfer and integration into the plant genome.

5) Multiple Cloning Regions (MCS) Permit and Facilitate the Insertion of One or More Nucleic Acid Sequences.

Also according to the invention are transgenic expression vectors which comprise the above-described transgenic expression cassettes. Vectors generally means structures which are capable of replication and which are preferably host-specific, and which make possible the uptake of nucleic acid sequences and their transfer into other cells. Examples of vectors can be plasmids, cosmids, phages, viruses or else *agrobacteria*. Vectors which are particularly suitable for the purposes of plant biotechnology are described hereinbelow.

Another subject of the invention relates to transgenic organisms, transformed with at least one transgenic expression cassette according to the invention or one transgenic expression vector according to the invention, and to cells, cell cultures, tissues, parts—such as, for example in the case of plant organisms, leaves, roots and the like—or propagation material derived from such organisms.

Organism, starting organisms or host organisms are understood as meaning prokaryotic or eukaryotic organisms such as, for example, microorganisms or plant organisms. Preferred microorganisms are bacteria, yeasts, algae or fungi.

Preferred bacteria are bacteria of the genus *Escherichia, Erwinia, Agrobacterium, Flavobacterium, Alcaligenes* or cyanobacteria, for example of the genus *Synechocystis*.

Especially preferred are microorganisms which are capable of infecting plants and thus of transferring the cassettes according to the invention. Preferred microorganisms are those from the genus *Agrobacterium* and in particular the species *Agrobacterium tumefaciens*.

Preferred yeasts are *Candida, Saccharomyces, Hansenula* or *Pichia*.

Preferred fungi are *Aspergillus, Trichoderma, Ashbya, Neurospora, Fusarium, Beauveria* or further fungi described in Indian Chem Engr. Section B. Vol 37, No 1,2 (1995) on page 15, Table 6.

Host or starting organisms which are preferred as transgenic organisms are, above all, plant organisms. Plant organisms generally means all those organisms which are capable of photosynthesis.

Included as plant organisms within the scope of the invention are all genera and species of the higher and lower plants of the plant kingdom. The mature plants, seeds, tubers, beets/swollen tap roots, fruits, shoots and seedlings and also parts, propagation material and cultures, for example cell cultures, derived therefrom are also included. Mature plants means plants at any developmental stage beyond the seedling. Seedling means a young immature plant in an early developmental stage.

Annual, perennial, monocotyledonous and dicotyledonous plants are preferred host organisms for preparing transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, *Hepaticae* (liverworts) and *Musci* (mosses); pteridophytes such as ferns, horsetail and club mosses; gymnosperms such as conifers, *cycades*, ginkgo and *Gnetalae*; algae such as *Chlorophyceae, Phaeophpyceae, Rhodophyceae, Myxophyceae, Xanthophyceae, Bacillariophyceae* (diatoms) and *Euglenophyceae*.

Preference is given to plants of the following plant families: Amaranthaceae, Asteraceae, Brassicaceae, carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanacea, Sterculiaceae, Tetragoniacea, Theaceae, Umbelliferae.

Preferred monocotyledonous plants are in particular selected from the monocotyledonous crop plants, for example of the Gramineae family, such as rice, corn, wheat, or other cereal species such as barley, malt, rye, triticale or oats, and also sugar cane and all grass species.

Preferred dicotyledonous plants are in particular selected from the dicotyledonous crop plants, for example Asteraceae such as sunflower, Tagetes or *Calendula* and others, Compositae, particularly the genus *Lactuca*, very particularly the species *sativa* (lettuce), and others, Cruciferae, particularly the genus *Brassica*, very particularly the species *napus* (oilseed rape), *campestris* (beet), *oleracea* cv *Tastie* (cabbage), *oleracea* cv Snowball Y (cauliflower) and *oleracea* cv Emperor (broccoli), and further cabbage species; and the genus *Arabidopsis*, very particularly the species *thaliana*, and also cress or canola, and others, Cucurbitaceae such as melon, pumpkin or zucchini, and others, Leguminosae particularly the genus *Glycine*, very particularly the species *max* (soybean), soya and also alfalfa, pea, bean plants or peanut, and others, Rubiaceae, preferably of the subclass Lamiidae, such as, for example, *Coffea arabica* or *Coffea liberica* (coffee bush), and others, Solanaceae, in particular the genus *Lycopersicon*, very particularly the species *esculentum* (tomato), and the genus *Solanum*, very particularly the species *tuberosum* (potato) and *melongena* (aubergine) and the genus *Capsicum*, very especially the species *annum* (pepper), and also tobacco, and others, Sterculiaceae, preferably of the subclass Dilleniidae, such as, for example, *Theobroma cacao* (cacao bush) and others, Theaceae, preferably of the subclass Dilleniidae, such as, for example, *Camellia sinensis* or *Thea sinensis* (tea shrub) and others, Umbelliferae, preferably the genus *Daucus*, very particularly the species *carota* (carrot), and Apium, very particularly the species *graveolens dulce* (celery), and others;

Chenopodiaceae, preferably the genus *Beta vulgaris*, in particular the species *Beta vulgaris* ssp. *vulgaris* var. *altissima* L. (sugar beet) and others;

and also linseed, cotton, hemp, flax, cucumber, spinach, carrot, sugar beet and the various tree, nut and vine species, in particular banana and kiwi fruit.

Plant organisms for the purposes of the invention are furthermore other photosynthetically active capable organisms, such as, for example, algae, and mosses. Preferred algae are green algae, such as, for example, algae of the genus *Haematococcus, Phaedactylum tricornatum, Volvox* or *Dunaliella.*

Most preferred are plants of the family Solanaceae, especially the genus *Lycopersicon*, very especially the species *esculentum* (tomato), the genus *Solanum*, very especially the species *tuberosum* (potato) and *melongena* (aubergine), of the family Chenopodiaceae, in particular the genus *Beta vulgaris*, in particular the species *Beta vulgaris* ssp. *vulgaris* var. *altissima L.* (sugar beet) and others, of the family Leguminosae, especially the genus *Glycine*, very especially the species *max* (soybean) and alfalfa, pea, bean plants, especially the genus *Vicia* or peanut and others, and other plants with starch-containing seeds, tubers, beets/swollen tap roots, fruits or tissues. Preferred among these, in turn, are tomato, potato, aubergine, soybean, alfalfa, pea, field bean, fodder beet, sugar beet and peanut.

The preparation of a transformed organism or of a transformed cell requires introducing the appropriate DNA into the appropriate host cell. A multiplicity of methods is available for this process which is referred to as transformation (see also Keown et al. 1990 Methods in Enzymology 185: 527-537). Thus, by way of example, the DNA may be introduced directly by microinjection or by bombardment with DNA-coated microparticles. The cell may also be permeabilized chemically, for example using polyethylene glycol, so that the DNA can enter the cell via diffusion. The DNA may also be performed via protoplast fusion with other DNA-containing units such as minicells, cells, lysosomes or liposomes. Another suitable method for introducing DNA is electroporation in which the cells are reversibly permeabilized by an electric impulse.

In the case of plants, the methods described for transforming and regenerating plants from plant tissues or plant cells are utilized for transient or stable transformation. Suitable methods are especially protoplast transformation by polyethylene glycol-induced DNA uptake, the biolistic method using the gene gun, the "particle bombardment" method, electroporation, the incubation of dry embryos in DNA-containing solution and microinjection.

Apart from these "direct" transformation techniques, a transformation may also be carried out by bacterial infection by means of *Agrobacterium tumefaciens* or *Agrobacterium rhizogenes*. These strains contain a plasmid (Ti or Ri plasmid), a part of which (what is known as T-DNA) is transferred to the plant after infection with *Agrobacterium* and integrated into the genome of the plant cell. The *Agrobacterium*-mediated transformation is best suited to dicotyledonous plant cells, whereas the direct transformation techniques are suitable for any cell type.

A transgenic expression cassette of the invention may be introduced advantageously into cells, preferably into plant cells, by using vectors.

In an advantageous embodiment, the transgenic expression cassette is introduced by means of plasmid vectors. Preference is given to those transgenic expression vectors which enable a stable integration of the transgenic expression cassette into the host genome. In this context, host genome means the entire hereditary information of the host and comprises for example not only the chromosomal DNA of the nucleus, but also the DNA of the plastids and mitochondria. However, the insertion into the chromosomal DNA of the nucleus is preferred.

In the case of injection or electroporation of DNA into plant cells, no particular demands on the plasmid used are made. It is possible to use simple plasmids such as those of the pUC series. If complete plants are to be regenerated from the transformed cells, it is necessary for an additional selectable marker gene to be present on the plasmid.

Transformation techniques have been described for various monocotyledonous and dicotyledonous plant organisms. Furthermore, various possible plasmid vectors which normally contain a replication origin for propagation in *E. coli* and a marker gene for selection of transformed bacteria are available for introducing foreign genes into plants. Examples are pBR322, pUC series, M13 mp series, pACYC184 etc.

The transgenic expression cassette may be introduced into the vector via a suitable restriction cleavage site. The resultant plasmid is first introduced into *E. coli*. Correctly transformed *E. coli* cells are selected, cultivated and the recombinant plasmid is obtained using methods familiar to the skilled worker. Restriction analysis and sequencing may be used in order to check the cloning step.

Transformed cells, i.e. those which contain the introduced DNA integrated into the DNA of the host cell may be selected from untransformed cells, if a selectable marker is part of the introduced DNA. A marker may be, by way of example, any gene which is capable of imparting a resistance to antibiotics or herbicides. Transformed cells which express such a marker gene are capable of surviving in the presence of concentrations of an appropriate antibiotic or herbicide, which kill an untransformed wild type. Examples are the bar gene which imparts resistance to the herbicide phosphinothricin (Rathore K S et al., Plant Mol Biol. 1993 March; 21(5):871-884), the nptII gene which imparts resistance to kanamycin, the hpt gene which imparts resistance to hygromycin and the EPSP gene which imparts resistance to the herbicide glyphosate.

Depending on the method of DNA introduction, further genes may be required on the vector plasmid. If *agrobacteria* are used, the transgenic expression cassette is to be integrated into specific plasmids, either into an intermediate vector (shuttle vector) or a binary vector. If, for example, a Ti or Ri plasmid is to be used for transformation, at least the right border, in most cases, however, the right and the left border, of the Ti or Ri plasmid T-DNA is connected as flanking region with the transgenic expression cassette to be introduced. Preference is given to using binary vectors. Binary vectors can replicate both in *E. coli* and in *Agrobacterium*. They normally contain a selection marker gene and a linker or polylinker flanked by the right and left T-DNA border sequences. They may be transformed directly into *Agrobacterium* (Holsters et al., Mol. Gen. Genet. 163 (1978), 181-187). The selection marker gene permits selection of transformed *agrobacteria*; an example is the nptII gene which imparts a resistance to kanamycin. The *Agrobacterium* which in this case acts as the host organism should already contain a plasmid with the vir region. This region is required for the transfer of T-DNA onto the plant cell. An *Agrobacterium* transformed in this way may be used for transformation of plant cells.

The use of T-DNA for transformation of plant cells has been intensely studied and described (B. Jenes et al., Techniques for Gene Transfer, in: Transgenic Plants, Vol. 1, Engineering and Utilization, edited by Kung S D and Wu R, Academic Press (1993), pp. 128-143 and in Potrykus (1991) Annu Rev Plant Physiol Plant Molec Biol 42:205-225; EP 120516; Hoekema, In: The Binary Plant Vector System, Offsetdrukkerij Kanters B. V., Alblasserdam, Chapter V; Fraley et al., Crit. Rev. Plant. Sci., 4:1-46 and An et al. (1985) EMBO J. 4:277-287). Various binary vectors are known and partly commercially available, such as, for example, pBIN19 (Bevan et al. (1984) Nucl Acids Res 12:8711f.; Clontech Laboratories, Inc. USA) or pSUN derivatives (SunGene GmbH & Co. KGaA; WO 02/00900). The expression cassette according to the invention can be inserted into these binary vectors and integrated into the plant genome as described hereinbelow.

The DNA is transferred into the plant cell by coculturing plant explants with *Agrobacterium tumefaciens* or *Agrobacterium rhizogenes*. Starting from infected plant material (e.g. leaf, root or stem parts, but also protoplasts or plant cell suspensions), it is possible to regenerate whole plants by using a suitable medium which may contain, for example, antibiotics or biocides for selection of transformed cells. The plants obtained may then be screened for the presence of the introduced DNA, in this case the transgenic expression cassette of the invention. As soon as the DNA has integrated into the host genome, the corresponding genotype is normally stable and the corresponding insertion is also found again in subsequent generations. Normally, the integrated transgenic expression cassette contains a selection marker which imparts to the transformed plant a resistance to a biocide (for example a herbicide), a metabolism inhibitor such as 2-DOG or an antibiotic such as kanamycin, G 418, bleomycin, hygromycin or phosphinothricin etc. The selection marker allows the selection of transformed cells from untransformed cells (McCormick et al. (1986) Plant Cell Reports 5:81-84). The plants obtained may be cultivated and crossed in the common manner. Two or more generations should be cultured in order to ensure that the genomic integration is stable and heritable.

As soon as a transformed plant cell has been prepared, it is possible to obtain a complete plant by using methods known to the skilled worker. To this end, callus cultures are used as starting point, by way of example. From these still undifferentiated cell masses, it is possible to induce formation of shoot and root in the known manner. The shoots obtained can be planted out and cultivated.

The integration of the T-DNA can be determined e.g. on the basis of the efficacy of expression of the nucleic acids to be expressed transgenically or of the selection marker for example in vitro by shoot meristem propagation using one of the above-described selection methods.

The invention further relates to cells, cell cultures, parts, such as, for example, roots, leaves, etc. in the case of transgenic plant organisms, and transgenic propagation material such as seeds, tubers, beets/swollen tap roots or fruits derived from the above-described transgenic organisms.

Genetically modified plants of the invention, which can be consumed by humans and animals, may also be used, for example directly or after preparation known per se, as foodstuffs or feedstuffs.

The invention further relates to the use of the above-described transgenic organisms of the invention and of the cells, cell cultures, parts, such as, for example, roots, leaves, etc., in the case of transgenic plant organisms, and transgenic propagation material such as seeds, tubers, beets/swollen tap roots or fruits derived from them for the production of food- or feedstuffs, pharmaceuticals or fine chemicals.

Preference is further given to a method for the recombinant production of pharmaceuticals or fine chemicals in host organisms, in which a host organism is transformed with one of the above-described transgenic expression cassettes or transgenic expression vectors and said transgenic expression cassette contains one or more structural genes which code for the fine chemical of interest or catalyze the biosynthesis of the fine chemical of interest, and the transformed host organism is cultivated and the fine chemical of interest is isolated from the cultivation medium. This method is broadly applicable for fine chemicals such as enzymes, vitamins, amino acids, sugars, fatty acids, natural and synthetic flavorings, aromatizing substances and colorants. Particular preference is given to the production of tocopherols and tocotrienols and also carotenoids. Cultivation of the transformed host organisms and isolation from said host organisms or from the cultivation medium are carried out by means of the methods known to the skilled worker. The production of pharmaceuticals such as, for example, antibodies or vaccines is described in Hood E E, Jilka J M (1999) Curr Opin Biotechnol 10(4):382-6; Ma J K, Vine N D (1999) Curr Top Microbiol Immunol 236:275-92.

Sequences

1. SEQ ID NO: 1 Promoter of the *Vicia faba* Pho1 gene
2. SEQ ID NO: 2 Promoter and 5'-untranslated region of the *Vicia faba* Pho1 gene
3. SEQ ID NO: 3 Promoter and 5'-untranslated region of the *Vicia faba* Pho1 gene and sequence encoding the transit peptide of the *Vicia faba* Pho1 protein
4. SEQ ID NO: 4 Oligonucleotide primer GP1 5'-GATTGTCTCTAGATGTAGGTGTGTTT-3'
5. SEQ ID NO: 5 Oligonucleotide primer GP2 5'-CATGGAAGCCATggTTGAATTTCT-3'
6. SEQ ID NO: 6 Oligonucleotide primer GPSP 5'-TTCCTGATCCaTGgCTTTCTGTTTCGC-3'
7. SEQ ID NO: 7 Nucleic acid sequence encoding the transit peptide of the *Vicia faba* plastidic 1,4-α-D-glucan:phosphate α-D-glucosyltransferase
8. SEQ ID NO: 8 Amino acid sequence encoding the transit peptide of the *Vicia faba* plastidic 1,4-α-D-glucan:phosphate α-D-glucosyltransferase

EXAMPLES

General Methods

Figure 1:
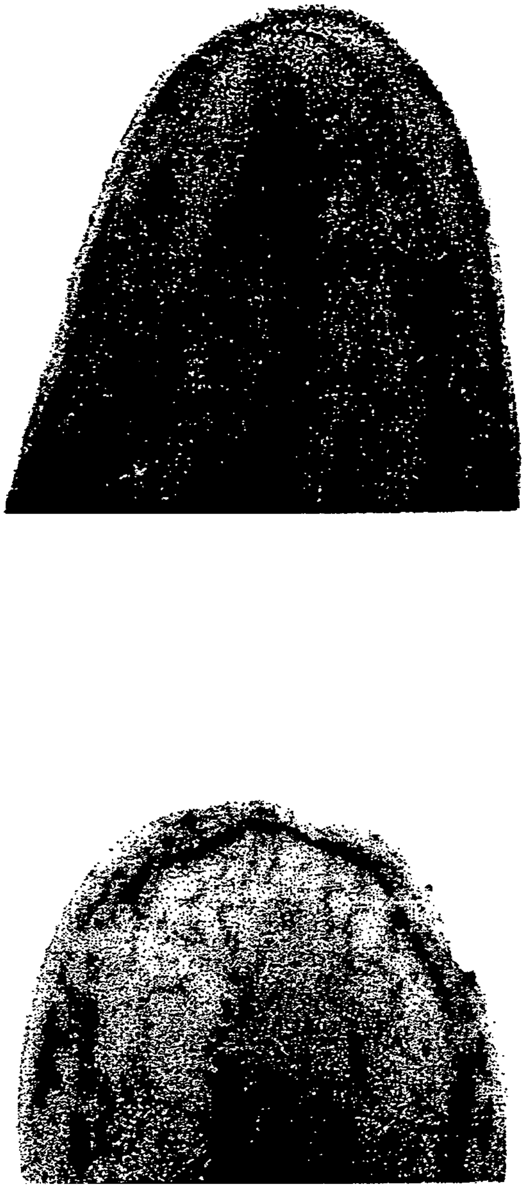
FIG. 1: Analysis of tubers of potato plants transformed with PTGPGUS-kan. What is shown is the staining of X-Gluc-incubated disks from tubers of two independent lines (A and B; the dark color corresponds to the blue staining).

Recombinant DNA techniques were carried out as described by Maniatis et al., Molecular Cloning—A Laboratory Manual (Cold Spring Harbor Lab., Cold Spring Harbor, N.Y., 1982). The enzymes employed were used as specified. The cloning vectors used were pUC18 (Yanisch-Perron C et al. (1985) Gene 33103-119), pBK-CMV (Stratagene) and pGUS1 (Pelemann J et al. (1989) Plant Cell 1:81-93). The vectors pGPTV-BAR and pGPTV-kan (Becker D et al. (1992) Plant Mol Biol 20:1195-1197) were employed for the transformation of plants. Strain DH5a (Hanahan D (1983) J Mol Biol 166:557-580) was used for the transformation into *E. coli*. The *agrobacteria* strains EHA 105, GV3101 [pMP90], C58C1 [pGV2260] and LBA4404 were transformed directly by means of the freeze-thaw method as described by An G (1987) Mol Gen Genet 207:210-216.

Example 1

Cloning the Promoter of the *Vicia faba* Glucan Phosphorylase

To isolate the promoter, genomic DNA of *Vicia faba* was cleaved with BlgII and ligated into the BamHI-cut ZAP Express Vector System (#239212) from Stratagene, and the phages were plated. A genomic *Vicia faba* DNA library (in pBKCMV (Stratagene)) was screened with a sample of the cDNA clone Pho1 (GenBank Acc. No.: Z36880) and the genomic clone pBKVfGP22 was isolated. Starting from the genomic clone pBKVfGP22, i) the 5'-flanking region including the 5'-untranslated region and the ATG start codon of the Pho1 gene and ii) the 5'-flanking region of the Pho1 gene including the putative transit peptide (Pho1-TP) were amplified.

a) PCR amplification of the Pho1 glucan phosphorylase promoter

```
Primer GP1 (SEQ ID NO: 4):
5'-GATTGTCTCTAGATGTAGGTGTGTTT-3'

Primer GP2 (SEQ ID NO: 5):
5'-CATGGAAGCCATggTTGAATTTCT-3'
```

The ATG start codon (reverse complement) is shown in primer GP2 in bold. By replacing two T by g (in lower case letters), the recognition site for the restriction enzyme NcoI Ort was introduced directly at the start codon.

Reaction Mix:

| | |
|---|---|
| 2 μl | pBKVfGP22 (1:500) |
| 10 μl | Ampli Taq buffer |
| 0.5 μl | Ampli Taq polymerase |
| 2 μl | dNTP (10 mM) |
| 2 μl | GP1 (10 μM) |
| 2 μl | GP2 (10 μM) |
| 81 μl | $H_2O$ |

PCR Conditions:

| | |
|---|---|
| 1 cycle: | 5 minutes at 96° C. |
| 25 cycles: | 0.5 minutes at 48° C.; 1 minute at 72° C.; 0.5 minutes at 96° C. |
| 1 cycle: | 0.5 minutes at 48° C.; 10 minutes at 72° C. |

b) PCR amplification of the glucan phosphorylase promoter including the transit peptide (Pho1-TP)

According to Buchner et al. (Planta 199:64-73, 1996), a sequence encoding a plastidic transit peptide is located at the N terminus of the transcript. This sequence shows no significant homologies with other chloroplastidic or amyloplastidic transit peptides. According to Gavel's and Heijne's rule (FEBS Lett 261:455-458, 1990), the sequence corresponds with the consensus of transit peptides. Accordingly, the transit peptide has a length of 64 amino acids. The primer GPSP was chosen in such a way that the environment of the cleavage site is retained owing to 10 additional amino acids, thus ensuring largely reliable processing of the transit peptides. The fragment was amplified with the primers GP1 (see hereinabove; SEQ ID NO: 4) and GPSP (SEQ ID NO: 6).

```
Primer GPSP (SEQ ID NO: 6):
5'-TTCCTGATCCaTGgCTTTCTGTTTCGC-3'
```

By replacing a T by a and A by g (lower case letters), the recognition site of the restriction enzyme NcoI was introduced.

Reaction Mix:

| | |
|---|---|
| 2 | μl pBKVfGP22 (1:500) |
| 10 | μl Ampli Taq buffer |
| 0.5 | μl Ampli Taq polymerase |
| 2 | μl dNTP (10 mM) |
| 2 | μl GP1 (10 μM) |
| 2 | μl GPSP (10 μM) |
| 81 | μl $H_2O$ |

PCR Conditions:

| | |
|---|---|
| 1 cycle: | 5 minutes at 96° C. |
| 25 cycles: | 0.5 minutes at 48° C.; 1 minute at 72° C.; 0.5 minutes at 96° C. |
| 1 cycle: | 0.5 minutes at 48° C.; 10 minutes at 72° C. |

The PCR products were purified and cloned into the vector pUC18 which had been cleaved with the restriction enzyme SmaI. The sequence of the resulting plasmids pGP and pGPSP2 was verified by sequence analysis.

Example 2

Construction of the Transgenic Expression Cassettes a) Construction of the Pho1-Promoter-GUS Expression Cassette The plasmid pGP was cleaved with the restriction enzymes PstI and NcoI. For the fusion with the GUS gene, the approx. 1.4 kb PstI/NcoI promoter fragment was cloned into the plasmid pGUS1 which had likewise been cleaved with PstI and NcoI, and the positive recombinants were identified by means of HindIII cleavage and sequence analysis. The resulting plasmid was named pGPGUS.

b) Construction of the Pho1-TP-Promoter-GUS Expression Cassette

The plasmid pGPSP2 was cleaved with the restriction enzymes PstI and NcoI. For the fusion with the GUS gene, the approx. 1.6 kb PstI/NcoI promoter fragment was cloned into the plasmid pGUS1 which had likewise been cleaved with PstI and NcoI, and the positive recombinants were identified by means of HindIII cleavage and sequence analysis. The resulting plasmid was named pGPSPGUS.

c) Cloning the Pho1-Promoter-GUS Expression Cassette into the Binary Vector pPTV-Bar The binary vector pGPTV-bar was cleaved with EcoRI and SmaI, made blunt-ended with Klenow enzyme and religated. The resulting plasmid pPTV-bar served as binary vector for the following constructions. The plasmid pGPGUS was cleaved with XbaI, and the fragment comprising the glucan phosphorylase promoter and the GUS gene was ligated into the XbaI-cut vector pPTV-bar. The resulting transgenic expression vector (plasmid) was named PTGPGUS.

d) Cloning the Pho1-TP-Promoter-GUS Expression Cassette into the Binary Vector pPTV-Bar The plasmid PGPSPGUS was cleaved with XbaI, and the fragment comprising the glucan phosphorylase promoter, the transit peptide and the GUS gene was ligated into the XbaI-cut vector pPTV-bar. The resulting transgenic expression vector (plasmid) was named PTGPSPGUS.

e) Preparation of the Plasmid PTGPGUSKan

To carry out the transformation into potato and tomato, the plasmid PTGPGUSKan was prepared. To this end, the binary vector pGPTV-kan was cleaved with EcoRI and SalI, and the EcoRI/SalI-cut fragment of the plasmid pGPGUS was cloned therein.

Example 3

Transformation of Tobacco, Oilseed Rape, *Arabidopsis*, Potato and Tomato a) Tobacco For the transformation of tobacco plants (*Nicotiana tabacum* L. cv. Samsun N N), 10 ml of an overnight culture of *Agrobacterium tumefaciens* EHA105, transformed with the transgenic expression vectors PTGPGUS and PTGPSPGUS, which culture had grown under selection conditions, were spun down, the supernatant was discarded, and the bacteria were resuspended in an equal volume of antibiotic-free medium. Leaf disks of sterile plants (diameter approx. 1 cm) were bathed in this bacterial solution in a sterile Petri dish. Thereafter, the leaf disks were plated in Petri dishes on MS medium (Murashige and Skoog (1962) Physiol Plant 15:473ff.) supplemented with 2% sucrose and 0.8% Bacto agar. Following incubation for two days in the dark at 25° C., they were transferred to MS medium supplemented with 100 mg/l kanamycin, 500 mg/l Claforan, 1 mg/l benzylaminopurine (BAP), 0.2 mg/l naphthylacetic acid (NAA), 1.6% glucose and 0.8% Bacto agar, and culturing was continued (16 hours light/8 hours dark). Growing shoots were transferred to hormone-free MS medium supplemented with 2% sucrose, 250 mg/l Claforan and 0.8% Bacto agar.

b) Oilseed Rape

Oilseed rape was transformed by means of the petiole transformation of Moloney et al. (Moloney MM et al. (1989) Plant Cell Reports 8:238-242). The *Agrobacterium* strain EHA105, transformed with the transgenic expression vector PTGPSPGUS, was employed for the generation of transgenic oilseed rape plants.

c) *Arabidopsis*

*Arabidopsis* was transformed by means of the floral dip method (Clough S J and Bent A F (1998) Plant J 16:735-743). The *Agrobacterium* strain EHA105, transformed with the transgenic expression vector PTGPSPGUS was employed for the generation of transgenic *Arabidopsis* plants.

d) Potato

For the transformation of potato (*Solanum tuberosum*), leaf disks of in-vitro plants were infected with *Agrobacterium tumefaciens* C58C1 [pGV2260], transformed with the transgenic expression vector PTGPGUSKan, in liquid Murashige Skoog medium for 20 minutes and subsequently cocultured for 2 days in the dark. After the coculture, the explants were cultured on solid MS medium which comprises 1.6% glucose instead of sucrose (MG) and which has been supplemented with 5 mg/l NAA, 0.1 mg/l BAP, 250 mg/l Timentin and 30 to 40 mg/l kanamycin (KIM) at 21° C. in a light/dark rhythm of 16 h/8 h. After this callus phase, the explants were placed on shoot induction medium (SIM). SIM had the following composition: MG supplemented with 2 mg/l zeatin riboside, 0.02 mg/l NAA, 0.02 mg/l GA3, 250 mg/l Timentin, 30 to 40 mg/l kanamycin. Every two weeks, the explants were transferred to fresh SIM. The shoots which formed were rooted on MS medium supplemented with 2% sucrose and 250 mg/l Timentin and 30 to 40 mg/l kanamycin.

e) Tomato

The starting explants for the transformation were cotyledons of seven- to ten-day-old seedlings of the line Microtom. The culture medium used for the germination is the medium of Murashige and Skoog (1962: Murashige and Skoog, 1962, Physiol Plant 15:473-) supplemented with 2% sucrose, pH 6.1. Germination takes place at 21° C. at a low light level (20-100 μE). After seven to ten days, the cotyledons are divided transversely and placed on the medium MSBN (MS, pH 6.1, 3% sucrose+1 mg/l BAP, 0.1 mg/l NAA), which has been charged on the previous day with tobacco cells grown in suspension culture. The tobacco cells are covered with sterile filter paper without leaving air bubbles. The preculture of the explants on the above-described medium is carried out for three to five days. Thereafter, the explants are infected with the *Agrobacterium tumefaciens* strain LBA4404, which bears the binary plasmid with the gene to be transformed, in the following manner: the strain which had been cultured overnight in YEB medium with the antibiotic for the binary plasmid at 28° C. is centrifuged. The bacterial pellet is resuspended in liquid MS medium (3% sucrose, pH 6.1) and brought to an optical density of 0.3 (at 600 nm). The precultured explants are suspended and incubated for 30 minutes at room temperature with gentle agitation. Thereafter, the explants are dried using sterile filter paper and returned to their preculture medium for three days of coculturing (21° C.).

After coculturing, the explants are transferred to MSZ2 medium (MS pH 6.1 supplemented with 3% sucrose, 2 mg/l zeatin, 100 mg/l kanamycin, 160 mg/l Timentin) and retained for the selective regeneration at 21° C. under low-light conditions (20-100 μE, photoperiod 16 h/8 h). The explants are transferred every two to three weeks until shoots form. Small shoots can be excised from the explant and rooted on MS (pH 6.1+3% sucrose) 160 mg/l Timentin, 30 mg/l kanamycin, 0.1 mg/l IAA. Rooted plants are transferred into the greenhouse.

Example 4

Isolation of Genomic DNA

The genomic DNA of transgenic tobacco, *Arabidopsis* and oilseed rape plants was isolated with the aid of the DNA isolation kit from Macherey & Nagel. In a first step, the transgenic lines were identified via PCR, using gene-specific primers. The integration of the foreign DNA was analyzed by means of Southern blot analyses of 201 g of DNA after a suitable restriction cleavage.

Example 5

Transient Expression Analysis of the Glucan Phosphorylase Promoter-GUS Cassettes A transient promoter analysis was carried out to assay the activity of the glucan phosphorylase promoter in different tissues and plants. This was done using the particle gun "Biolistic PDS-1000 System (BioRad Laboratories, Hercules, Calif.) with a vacuum of 27 mmHg. The microcarriers used were gold particles with a diameter of 1.0 μm, which were coated with plasmid DNA as specified by BioRad. To this end, 25 μl of a gold suspension (50 mg/ml) were mixed with 10 μl of Qiagen-purified plasmid DNA (1 μg/μl), 25 μl $CaCl_2$ (2.5 M) and 10 μl spermidine (0.1 M), left to stand briefly and then spun down. The coated gold particles were washed with 70% and 100% ethanol. Embryos were bombarded with 2000 PSI, fruits of tomatoes and tubers of potatoes with 1800 PSI. The bombarded tissues were cultured for 36 hours in liquid medium and then treated overnight at 37° C. with an X-Gluc solution. The blue spots were counted.

After the bombardment with the plasmids pGPGUS and PGPSPGUS, no, or barely visible, spots were found in the embryos of oilseed rape, sunflower, linseed, *Vicia faba* and soybean. The bombardment of disks of the potato tuber and fruit tissue of tomatoes resulted in markedly more spots; no substantial differences between the plasmids were observed. A plasmid which comprises the GUS gene under the control of the USP (unknown seed protein; Baumlein et al. (1991) Mol Gen Genet 225:459-467) was used as control. Although the promoter brings about a seed-specific expression, a multiplicity of blue spots were also observed in other sink tissues.

Example 6

Detection of the Tissue-Specific Expression

To determine the characteristics of the promoter, it is necessary to place the promoter before what is known as a reporter gene, which makes possible a determination of the expression activity. An example which may be mentioned is the bacterial β-glucuronidase (Jefferson et al. (1987) EMBO J. 6:3901-3907). The β-glucuronidase activity can be determined in planta by means of a chromogenic substrate such as 5-bromo-4-chloro-3-indolyl-β-D-glucuronic acid (X-Gluc) in connection with an activity staining. To examine the tissue specificity, the plant tissue is prepared and stained. It is particularly advantageous to excise embryos from immature or mature seeds before staining them. Likewise, unopened flowers can be stained to detect a promoter activity in the pollen.

A second assay permits a quantitative determination of the GUS activity in the test tissue. β-Glucuronidase MUG (4-methylumbelliferyl-β-D-glucuronide) is used as substrate for the quantitative activity determination; the former is cleaved into MU (methylumbelliferone) and glucuronic acid.

High-level expression of the glucan phosphorylase promoter was detected in the tubers of the analyzed potato plants which had been transformed with the plasmid PTGPGUS-kan. FIG. 1 shows the GUS activity in disks of tubers from two lines. Apart from 2 lines, where there was barely discernible expression in the leaves, nothing was found that suggested expression in the leaves. Again, the correlation of the expression in starch-containing tissues is shown.

Figure 2:
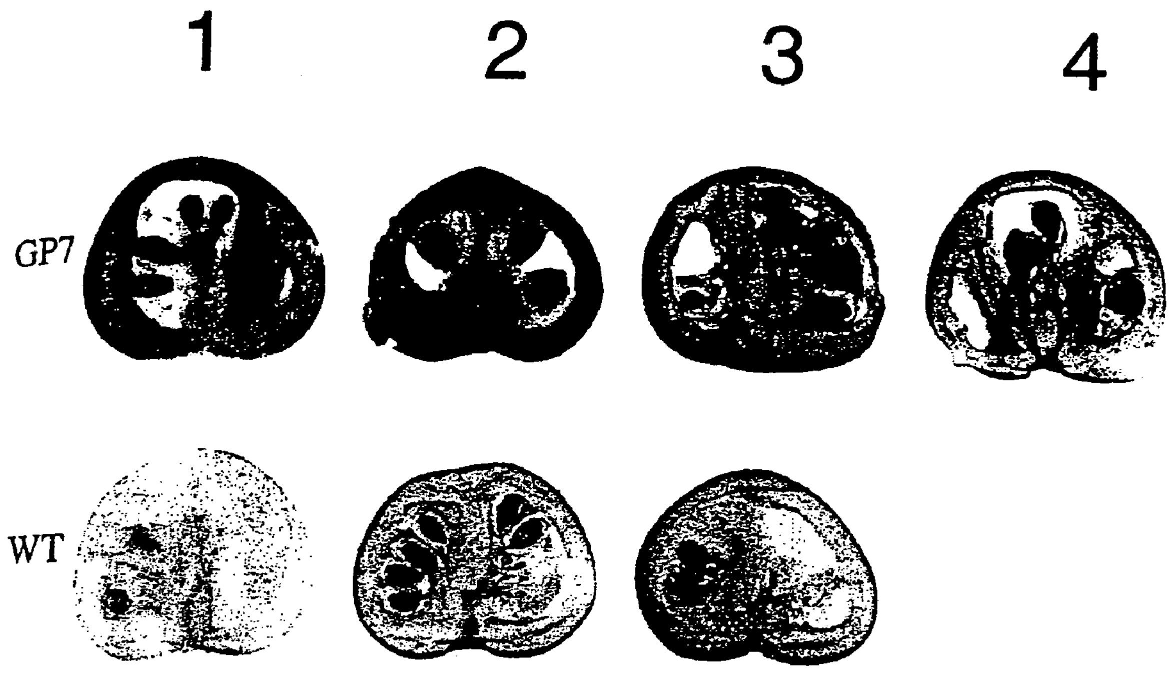
FIG. 2: Analysis of fruits of tomato plants transformed with PTGPGUS-kan. What is shown are fruits of a transgenic line (gp7) in comparison with wild-type fruits. The dark color of the transgenic fruits corresponds to the GUS blue staining. The dark color of the wild-type fruits corresponds to the natural red coloration of the fruits; here, no blue staining can be found. 1: green, immature fruit; 2: orange-colored fruit; 3: red, mature fruit; 4: overripe fruit. It can be seen that the blue staining decreases as the degree of maturation of the fruit increases.
Figure 3:
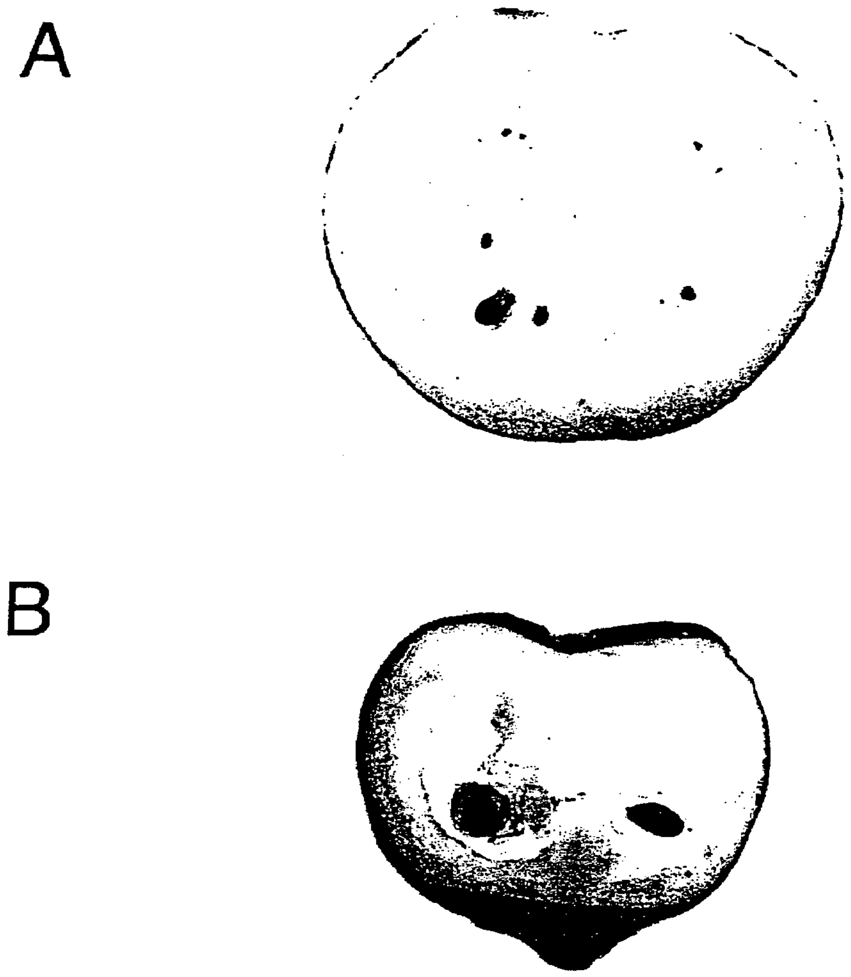
FIG. 3: Analysis of fruits of tomato plants transformed with PTUSPGUS-kan. A: immature fruit; B: mature fruit. In contrast with the promoters according to the invention, the USP promoter is only active in the seed kernels.
Figure 4:
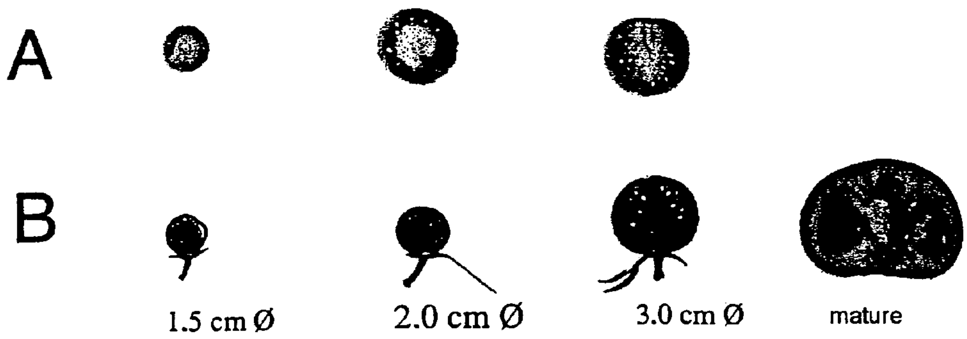
FIG. 4: Starch staining of tomato disks in different develop ental stages. Top row (A) unstained; bottom row (B) starch staining with Lugol's solution. It can be seen that the staining decreases with an increasing degree of maturity of the fruit.

High-level glucuronidase expression was detected in the fruits of the transgenic tomato plants which had been transformed with the plasmid PTGPGUS-kan. FIG. 2 shows the high-level expression during the development of the tomato fruit. In contrast, the PTUSPGUSkan plants, which had been generated for comparison purposes, showed no further activities of this promoter in the fruits of the transgenic tomato plants, besides a high level of seed-specific activity (FIG. 3).

No substantial activity of the glucan phosphorylase promoter was detected in tobacco, oilseed rape and *Arabidopsis*.

Example 7

Figure 5:
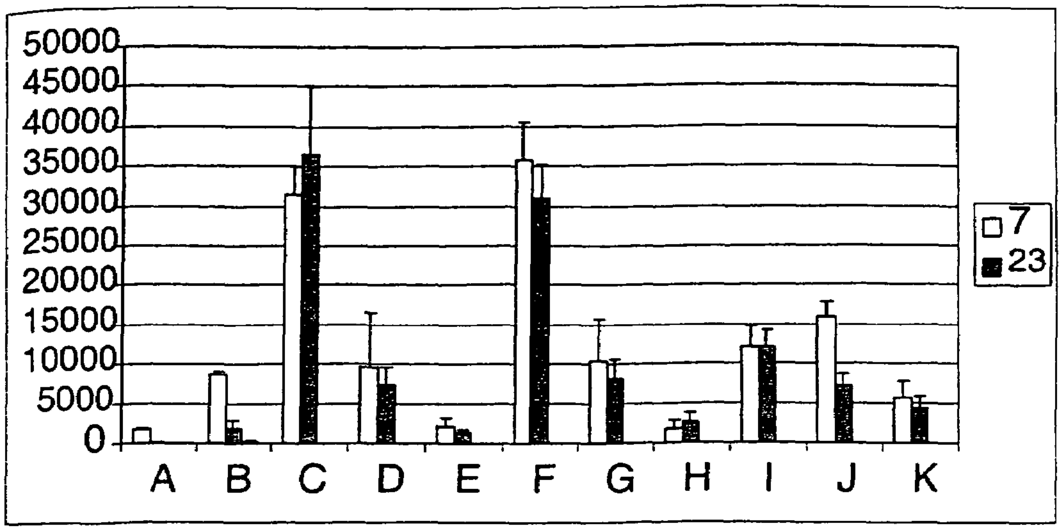
FIG. 5: Analysis of fruits of tomato plants transformed with PTGPGUS-kan. What is shown are the GUS expression activities in tissues from two transgenic lines (7 and 23). Wild-type fruits showed in each case only one background level. A: leaf; B: root; C: skin, green; D: skin, orange; E: skin, red; F: flesh, green; G: flesh, orange; H: flesh, red; I: seeds, green; J: seeds, orange; K: seeds, red. A high activity is discernible in particular in the immature flesh and skin of tomatoes (Y axis: GUS activity measured in pM MU/min mg protein; MU: methylumbelliferone). It can be seen that the GUS activity decreases with increasing degree of maturity of the fruit.

Correlation of Starch Content and Expression Pattern of the Glucan Phosphorylase Promoter in Tomato Fruits To demonstrate the correlation between starch-containing tissue and expression of the glucan phosphorylase promoter, tomato disks were stained with Lugol's solution. Intense blue staining shows the distribution of starch. As can be seen from FIG. 5, it is precisely in the young tomato fruits that a large amount of starch is detected. The distribution pattern also agrees with the GUS expression pattern of the transgenic fruits.

What is claimed is:

1. A method for directing transgenic expression of a nucleic acid sequence in carbohydrate-storing sink tissues of plants, which comprises the following steps:

I. introducing, into plant cells, a transgenic expression cassette, wherein the transgenic expression cassette comprises at least the following elements:

a) the promoter sequence of the gene encoding the *Vicia faba* plastidic 1,4-α-D-glucan:phosphate α-D-glucosyltransferase, or a fragment thereof having the same promoter activity, and b) at least one further nucleic acid sequence, wherein the promoter sequence or the fragment thereof and the at least one further nucleic acid sequence are functionally linked together, and the further nucleic acid sequence is heterologous in relation to the promoter sequence, II. selecting transgenic cells which comprise said expression cassette stably integrated into the genome, and III. regenerating intact plants from said transgenic cells, wherein the promoter sequence or the fragment thereof directs expression of the further nucleic acid sequence in carbohydrate-storing sink tissue, but essentially not in source tissues.

2. The method according to claim 1, wherein the promoter sequence comprises i) the nucleotide sequence of SEQ ID NO: 1, or ii) a fragment of SEQ ID NO: 1 which directs expression of a nucleic acid sequence in carbohydrate-storing sink tissues of plants.

3. An isolated nucleic acid sequence comprising:

i) the promoter sequence of the gene of the *Vicia faba* plastidic 1,4-α-D -glucan:phosphate α-D-glucosyltransferase of SEQ ID NO: 1, or ii) a fragment of SEQ ID NO: 1 which directs expression of a nucleic acid sequence in carbohydrate-storing sink tissues of plants.

4. The isolated nucleic acid sequence according to claim 3, further comprising a nucleotide sequence encoding a transit peptide located in 3' orientation to the promoter sequence or the fragment thereof.

5. The isolated nucleic acid sequence according to claim 4, wherein the nucleotide sequence encoding a transit peptide is the sequence of SEQ ID NO: 8.

6. The isolated nucleic acid sequence according to claim 3, wherein the nucleic acid sequence is the sequence of SEQ ID NO: 2 or 3.

7. A transgenic expression cassette for the expression of a nucleic acid comprising:

a) the promoter sequence of the gene encoding the *Vicia faba* plastidic 1,4-α-D-glucan:phosphate α-D-glucosyltransferase, or a fragment thereof having the same promoter activity, and b) at least one further nucleic acid sequence, wherein the promoter sequence or the fragment thereof and the at least one further nucleic acid sequence are functionally linked together, and the further nucleic acid sequence is heterologous in relation to the promoter sequence or the fragment thereof; and wherein the promoter sequence or the fragment thereof directs expression of the further nucleic acid sequence in carbohydrate-storing sink tissue, but essentially not in source tissues.

8. The transgenic expression cassette according to claim 7, wherein the promoter sequence comprises i) the nucleotide sequence of SEQ ID NO: 1, or ii) a fragment of SEQ ID NO: 1 which directs expression of a nucleic acid sequence in carbohydrate-storing sink tissues of plants.

9. The transgenic expression cassette according to claim 8, where the promoter sequence is the sequence of SEQ ID NO: 2 or 3.

10. The transgenic expression cassette according to claim 7, wherein the at least one further nucleic acid sequence a) encodes a protein, or b) transcribes a sense RNA, antisense RNA or double-stranded RNA.

11. A transgenic expression vector comprising the nucleic acid sequence according to claim 3.

12. A transgenic organism transformed with the trausgenic expression cassette according to claim 7.

13. The transgenic organism according to claim 12, selected from the group consisting of bacteria, yeasts, fungi, nonhuman animal organisms and plant organisms.

14. The transgenic organism according to claim 12, selected from the group consisting of tomato, potato, aubergine, soybean, alfalfa, pea, field bean, fodder beet, sugar beet and peanut.

15. A cell culture, part, organ, tissue or transgenic propagation material derived from the transgenic organism according to claim 12.

16. A method for the transgenic expression of a nucleic acid comprising growing or culturing the transgenic organism according to claim 12 or cell cultures, parts, organs, tissues or transgenic propagation material derived therefrom.

17. A method for the production of foodstuffs, feedstuffs, seed, pharmaceuticals or fine chemicals, in which the transgenic organism according to claim 12 is cultured and the desired foodstuff, feedstuff, seed, pharmaceutical or fine chemical is produced and/or isolated using said organism.

18. The method of claim 1, wherein the transgenic expression cassette further comprises one or more genetic control elements.

19. The transgenic expression cassette of claim 7, wherein the expression cassette further comprises one or more genetic control elements.

20. A method for identifying and/or isolating a sequence which directs expression in carbohydrate-storing sink tissue, but essentially not in source tissues comprising preparing fragments of the nucleic acid sequence of SEQ ID NO: 1;

testing the fragments obtained for carbohydrate-storing sink tissue expression; and identifying and/or isolating a fragment with carbohydrate-storing sink tissue expression activity.

21. An expression cassette for carbohydrate-storing sink tissue, but essentially not source tissues, expression in plants comprising at least one transcription regulating nucleotide sequence, wherein the transcription regulating nucleotide sequence comprises a fragment obtained by the method of claim 20.

22. The expression cassette of claim 21, further comprising at least one nucleic acid sequence which is operably linked to and heterologous in relation to said transcription regulating nucleotide sequence, wherein the transcription regulating nucleotide sequence directs expression of the further nucleic acid sequence in carbohydrate-storing sink tissue, but essentially not in source tissues.

23. An expression cassette for carbohydrate-storing sink tissue, but essentially not source tissues, expression in plants comprising i) at least one transcription regulating nucleotide sequence, and ii) at least one further nucleic acid sequence which is operably linked to and heterologous in relation to said transcription regulating nucleotide sequence, wherein the transcription regulating nucleotide sequence comprises the nucleotide sequence described by SEQ ID NOs: 1, 2, or 3, or a fragment thereof having the same promoter activity as the nucleotide sequence of SEQ ID NO: 1, 2, or 3;

and wherein the transcription regulating nucleotide sequence directs expression of the further nucleic acid sequence in carbohydrate-storing sink tissue, but essentially not in source tissues.

24. A method for directing carbohydrate-storing sink tissue expression in a plant comprising:

I. introducing into a plant cell the expression cassette of claim 23,

II. selecting a transgenic cell which comprise said expression cassette, and

III. regenerating a plant from the transgenic cell, wherein the transcription regulating nucleotide sequence directs carbohydrate-storing sink tissue, but essentially not in source tissues, expression of the operably linked nucleic acid sequence in the plant.

* * * * *

UNITED STATES PATENT AND TRADEMARK OFFICE

CERTIFICATE OF CORRECTION

PATENT NO. : 7,589,254 B2
APPLICATION NO. : 10/527375
DATED : September 15, 2009
INVENTOR(S) : Ute Heim et al.

It is certified that error appears in the above-identified patent and that said Letters Patent is hereby corrected as shown below:

Title Page, Item (56) in the References Cited:

In Foreign Patent Documents at page 1, left column, “WO-00/26338” should read -- WO-00/26388 --.

In Other Publications at page 1, right column, “Deickmann, Jill et al., “Ineraction Of A DNA Binding Factor With” should read -- Deikman, Jill et al., “Interaction Of A DNA Binding Factor With --

In the Claims:

In Claim 12, in column 45, on line 46, “12. A transgenic organism transformed with the trausgenic” should read -- 12. A transgenic organism transformed with the transgenic --.

Signed and Sealed this

Seventeenth Day of November, 2009

David J. Kappos
*Director of the United States Patent and Trademark Office*

UNITED STATES PATENT AND TRADEMARK OFFICE

CERTIFICATE OF CORRECTION

PATENT NO. : 7,589,254 B2
APPLICATION NO. : 10/527375
DATED : September 15, 2009
INVENTOR(S) : Heim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 466 days.

Signed and Sealed this

Twenty-first Day of September, 2010

David J. Kappos

David J. Kappos
*Director of the United States Patent and Trademark Office*

SEQUENCE LISTING

<160> NUMBER OF SEQ ID NOS: 8

<210> SEQ ID NO 1
<211> LENGTH: 1300
<212> TYPE: DNA
<213> ORGANISM: Vicia faba
<220> FEATURE:
<221> NAME/KEY: promoter
<222> LOCATION: (1)..(1300)

<400> SEQUENCE: 1

```
gattgtctct agatgtaggt gtggttttat cgaactgagt taacagactt tgtgtgttct      60

ttatttcttt tgtcttgaat tattgttact gtcatattgt gtgttatttg atttaacaag     120

taaaactatc tgatttaaca agtaaagcaa gttattatag acatcttttc caacatctgt     180

cccgtgagaa acaaaattat aacttggaag acttgaatta aggtggtgtc ttgaaaaaat     240

aatatacttc gtcagtgcaa catgttgcag taaatgtgca acaggttaca ccccttcatt     300

gcaatgttca atttcagaca gagatttggc acaataagtt gcagtaaatg tgtaacatgt     360

tgcaccattc cagctttata ctttttgaga caaagaatta gtgcaatcaa ttataggtat     420

gagaaactta tttttctcat tagttggtca gctgtactat ttgtatgata gtttaaatat     480

caagttggat catttatgtt ataatgccat ctttccttcc taattctctc tatttctctc     540

attatctcaa tctttctatt attcactatt gttttcgtga ttgaaatttt aatccaacaa     600

ataaatgaaa acgcaacaca attgataaaa tacatcaaac ttaagttaaa ggtgtaagtt     660

tgagtcttga tttagtataa aattttatct atcaacatta taatttatta attttaaatt     720

ttttattatt tatatattta caaatacaat ttctgattta aatataataa ataacattaa     780

aaatatattt ttaaataaca ttatataaat tatgtgacgt aacaccaaat gattattgtc     840

atatcaatat cacgccataa attatgggat caactatata aatttgaaga ggataaaaag     900

aaggaaaaaa aatattaaat ataggaaaaa actgtttttt taaaaggact aaagttttgt     960

atatcaaaat caaaatcaaa attgaaatta aaatttcatt tttatattaa aaacaaaaaa    1020

aaagcttgag tttaatttta aacacaagtc aatattcttc tccaagtgta aaaactcaca    1080

atcggcgctt tttaaaggaa aaaatgactt ttcacgaccc gcgtttggag gtgctgtaac    1140

gtggcaataa gtcacgaaag agcgtgcgtg gtagtacaaa aaaaactaaa atccagaagc    1200

taaaagctcg tgattcgatg ccacatcata ttctttttca acactagtaa gagtacagtg    1260

tagaatacaa aacaccacct ctattataga gagaagaggt                          1300
```

<210> SEQ ID NO 2
<211> LENGTH: 1360
<212> TYPE: DNA
<213> ORGANISM: Vicia faba
<220> FEATURE:
<221> NAME/KEY: promoter
<222> LOCATION: (1)..(1300)
<220> FEATURE:
<221> NAME/KEY: 5'UTR
<222> LOCATION: (1301)..(1357)
<220> FEATURE:
<221> NAME/KEY: misc_feature
<222> LOCATION: (1358)..(1360)
<223> OTHER INFORMATION: ATG-Start-Codon -continued

<400> SEQUENCE: 2

```
gattgtctct agatgtaggt gtggttttat cgaactgagt taacagactt tgtgtgttct     60
ttatttcttt tgtcttgaat tattgttact gtcatattgt gtgttatttg atttaacaag    120
taaaactatc tgatttaaca agtaaagcaa gttattatag acatcttttc caacatctgt    180
cccgtgagaa acaaaattat aacttggaag acttgaatta aggtggtgtc ttgaaaaaat    240
aatatacttc gtcagtgcaa catgttgcag taaatgtgca acaggttaca ccccttcatt    300
gcaatgttca atttcagaca gagatttggc acaataagtt gcagtaaatg tgtaacatgt    360
tgcaccattc cagctttata ctttttgaga caaagaatta gtgcaatcaa ttataggtat    420
gagaaactta tttttctcat tagttggtca gctgtactat ttgtatgata gtttaaatat    480
caagttggat catttatgtt ataatgccat ctttccttcc taattctctc tatttctctc    540
attatctcaa tctttctatt attcactatt gttttcgtga ttgaaatttt aatccaacaa    600
ataaatgaaa acgcaacaca attgataaaa tacatcaaac ttaagttaaa ggtgtaagtt    660
tgagtcttga tttagtataa aattttatct atcaacatta taatttatta attttaaatt    720
ttttattatt tatatattta caaatacaat ttctgattta aatataataa ataacattaa    780
aaatatattt ttaaataaca ttatataaat tatgtgacgt aacaccaaat gattattgtc    840
atatcaatat cacgccataa attatgggat caactatata aatttgaaga ggataaaaag    900
aaggaaaaaa aatattaaat ataggaaaaa actgtttttt taaaaggact aaagttttgt    960
atatcaaaat caaaatcaaa attgaaatta aaatttcatt tttatattaa aaacaaaaaa   1020
aaagcttgag tttaatttta aacacaagtc aatattcttc tccaagtgta aaaactcaca   1080
atcggcgctt tttaaaggaa aaaatgactt ttcacgaccc gcgtttggag gtgctgtaac   1140
gtggcaataa gtcacgaaag agcgtgcgtg gtagtacaaa aaaaactaaa atccagaagc   1200
taaaagctcg tgattcgatg ccacatcata ttctttttca acactagtaa gagtacagtg   1260
tagaatacaa aacaccacct ctattataga gagaagaggt acaatacaaa caatcaaagc   1320
tctgtgagtg tgtgagtgag tgagagaaat tccaaccatg                         1360
```

<210> SEQ ID NO 3
<211> LENGTH: 1582
<212> TYPE: DNA
<213> ORGANISM: Vicia faba
<220> FEATURE:
<221> NAME/KEY: promoter
<222> LOCATION: (1)..(1300)
<220> FEATURE:
<221> NAME/KEY: 5'UTR
<222> LOCATION: (1301)..(1357)
<220> FEATURE:
<221> NAME/KEY: transit_peptide
<222> LOCATION: (1358)..(1582)

<400> SEQUENCE: 3

```
gattgtctct agatgtaggt gtggttttat cgaactgagt taacagactt tgtgtgttct     60
ttatttcttt tgtcttgaat tattgttact gtcatattgt gtgttatttg atttaacaag    120
taaaactatc tgatttaaca agtaaagcaa gttattatag acatcttttc caacatctgt    180
cccgtgagaa acaaaattat aacttggaag acttgaatta aggtggtgtc ttgaaaaaat    240
aatatacttc gtcagtgcaa catgttgcag taaatgtgca acaggttaca ccccttcatt    300
gcaatgttca atttcagaca gagatttggc acaataagtt gcagtaaatg tgtaacatgt    360
tgcaccattc cagctttata ctttttgaga caaagaatta gtgcaatcaa ttataggtat    420
```

-continued

```
gagaaactta tttttctcat tagttggtca gctgtactat ttgtatgata gtttaaatat    480

caagttggat catttatgtt ataatgccat ctttccttcc taattctctc tatttctctc    540

attatctcaa tctttctatt attcactatt gttttcgtga ttgaaatttt aatccaacaa    600

ataaatgaaa acgcaacaca attgataaaa tacatcaaac ttaagttaaa ggtgtaagtt    660

tgagtcttga tttagtataa aattttatct atcaacatta taatttatta attttaaatt    720

ttttattatt tatatattta caaatacaat ttctgattta aatataataa ataacattga    780

aaatatattt ttaaataaca ttatataaat tatgtgacgt aacaccaaat gattattgtc    840

atatcaatat cacgccataa attatgggat caactatata aatttgaaga ggataaaaag    900

aaggaaaaaa aatattaaat ataggaaaaa actgtttttt taaaaggact aaagttttgt    960

atatcaaaat caaaatcaaa attgaaatta aaatttcatt tttatattaa aaacaaaaaa   1020

aaagcttgag tttaatttta aacacaagtc aatattcttc tccaagtgta aaaactcaca   1080

atcggcgctt tttaaaggaa aaaatgactt ttcacgaccc gcgtttggag gtgctgtaac   1140

gtggcaataa gtcacgaaag agcgtgcgtg gtagtacaaa aaaaactaaa atccagaagc   1200

taaaagctcg tgattcgatg ccacatcata ttctttttca acactagtaa gagtacagtg   1260

tagaatacaa aacaccacct ctattataga gagaagaggt acaatacaaa caatcaaagc   1320

tctgtgagtg tgtgagtgag tgagagaaat tccaattatg gcttccatga caatgcggtt   1380

tcatccaaat tccaccgccg taaccgaatc cgttcctcgc cgtggctccg tttacggatt   1440

catcggttac agatcctcgt cgttgttcgt ccgaacgaac gttatcaagt atcgttctgt   1500

taagcgtaat ctggaattta ggaggagaag cgctttctct gtgaagtgtg gttctggtaa   1560

tgaagcgaaa cagaaagcca tg                                            1582
```

<210> SEQ ID NO 4
<211> LENGTH: 26
<212> TYPE: DNA
<213> ORGANISM: Artificial sequence
<220> FEATURE:
<223> OTHER INFORMATION: Description of the artificial sequence: Oligonucleotide primer

<400> SEQUENCE: 4

```
gattgtctct agatgtaggt gtgttt                                          26
```

<210> SEQ ID NO 5
<211> LENGTH: 24
<212> TYPE: DNA
<213> ORGANISM: Artificial sequence
<220> FEATURE:
<223> OTHER INFORMATION: Description of the artificial sequence: Oligonucleotide primer

<400> SEQUENCE: 5

```
catggaagcc atggttgaat ttct                                            24
```

<210> SEQ ID NO 6
<211> LENGTH: 27
<212> TYPE: DNA
<213> ORGANISM: Artificial sequence
<220> FEATURE:
<223> OTHER INFORMATION: Description of the artificial sequence: Oligonucleotide primer

<400> SEQUENCE: 6

```
ttcctgatcc atggctttct gtttcgc                                         27
```

-continued

```
<210> SEQ ID NO 7
<211> LENGTH: 225
<212> TYPE: DNA
<213> ORGANISM: Vicia faba
<220> FEATURE:
<221> NAME/KEY: transit_peptide
<222> LOCATION: (1)..(225)
<220> FEATURE:
<221> NAME/KEY: CDS
<222> LOCATION: (1)..(225)

<400> SEQUENCE: 7

atg gct tcc atg aca atg cgg ttt cat cca aat tcc acc gcc gta acc       48
Met Ala Ser Met Thr Met Arg Phe His Pro Asn Ser Thr Ala Val Thr
  1               5                  10                  15

gaa tcc gtt cct cgc cgt ggc tcc gtt tac gga ttc atc ggt tac aga       96
Glu Ser Val Pro Arg Arg Gly Ser Val Tyr Gly Phe Ile Gly Tyr Arg
             20                  25                  30

tcc tcg tcg ttg ttc gtc cga acg aac gtt atc aag tat cgt tct gtt      144
Ser Ser Ser Leu Phe Val Arg Thr Asn Val Ile Lys Tyr Arg Ser Val
         35                  40                  45

aag cgt aat ctg gaa ttt agg agg aga agc gct ttc tct gtg aag tgt      192
Lys Arg Asn Leu Glu Phe Arg Arg Arg Ser Ala Phe Ser Val Lys Cys
     50                  55                  60

ggt tct ggt aat gaa gcg aaa cag aaa gcc atg                          225
Gly Ser Gly Asn Glu Ala Lys Gln Lys Ala Met
 65                  70                  75


<210> SEQ ID NO 8
<211> LENGTH: 75
<212> TYPE: PRT
<213> ORGANISM: Vicia faba

<400> SEQUENCE: 8

Met Ala Ser Met Thr Met Arg Phe His Pro Asn Ser Thr Ala Val Thr
  1               5                  10                  15

Glu Ser Val Pro Arg Arg Gly Ser Val Tyr Gly Phe Ile Gly Tyr Arg
             20                  25                  30

Ser Ser Ser Leu Phe Val Arg Thr Asn Val Ile Lys Tyr Arg Ser Val
         35                  40                  45

Lys Arg Asn Leu Glu Phe Arg Arg Arg Ser Ala Phe Ser Val Lys Cys
     50                  55                  60

Gly Ser Gly Asn Glu Ala Lys Gln Lys Ala Met
 65                  70                  75
```